(12) United States Patent
Lau

(10) Patent No.: US 7,417,238 B2
(45) Date of Patent: Aug. 26, 2008

(54) DEVICE FOR MEASURING LIGHT-ACTIVATED FLUORESCENCE AND ITS USE

(75) Inventor: Matthias Lau, Dresden (DE)

(73) Assignee: Uwe Kirschner, Dresden (DE)

( * ) Notice: Subject to any disclaimer, the term of this patent is extended or adjusted under 35 U.S.C. 154(b) by 110 days.

(21) Appl. No.: 11/143,145

(22) Filed: Jun. 2, 2005

(65) Prior Publication Data

US 2006/0175555 A1    Aug. 10, 2006

Related U.S. Application Data

(63) Continuation of application No. 11/052,399, filed on Feb. 7, 2005, now abandoned, which is a continuation-in-part of application No. 09/423,534, filed on Dec. 14, 1999.

(51) Int. Cl.
    *G01N 21/64*    (2006.01)
(52) U.S. Cl. .................................................. 250/486.1
(58) Field of Classification Search .............. 250/486.1, 250/484.4, 458.1, 227.14, 573, 341.1, 341.6
    See application file for complete search history.

(56) References Cited

U.S. PATENT DOCUMENTS

| | | | | |
|---|---|---|---|---|
| 4,431,004 A | * | 2/1984 | Bessman et al. ............ 600/347 |
| 4,548,907 A | * | 10/1985 | Seitz et al. ................... 436/163 |
| 5,001,054 A | * | 3/1991 | Wagner ........................ 435/14 |
| 5,319,975 A | * | 6/1994 | Pederson et al. .......... 73/335.01 |
| 5,606,170 A | * | 2/1997 | Saaski et al. ............. 250/458.1 |
| 6,066,245 A | * | 5/2000 | Trost ........................... 204/461 |

* cited by examiner

*Primary Examiner*—David P. Porta
*Assistant Examiner*—Marcus H Taningco
(74) *Attorney, Agent, or Firm*—Marshall & Melhorn LLC

(57) ABSTRACT

The invention relates to a device for measuring light-activated fluorescence of at least one coating that contains a fluorescent material, and its use for measuring fluid materials which cause fluorescence-quenching in at least one of the fluorescent coatings. To activate the fluorescence, at least one first light wave-guide is directed onto at least one coating applied to a support and the fluorescent light is directed at a detector by means of at least one one-second light wave-guide, in order to determine the intensity of the fluorescent light. The end faces of the different fluorescent light wave guides are then arranged to have overlapping entry and/or exit cones and/or be of a shape substantially identical to the at least one coating containing a fluorescent material, in such a way that an accurate measurement of the fluorescence intensity can be attained, and that the light source(s), light wave guides and the detector(s) are lodged in a measuring head.

48 Claims, 19 Drawing Sheets

DEVICE FOR MEASURING LIGHT-ACTIVATED FLUORESCENCE AND ITS USE

CROSS REFERENCE TO RELATED APPLICATIONS

This application is a continuation-in-part of U.S. patent application Ser. No.11/052,399 filed Feb. 7, 2005, now abandoned which is a continuation-in-part of application Ser. No. 09/423,534 filed Dec. 14, 1999, which is a U.S. national stage application off of International, Application PCT/DE98/01316, filed May 12, 1998. U.S. patent application Ser. No. 11/052,399 was pending as of the filing date of the present application. The contents of U.S. patent application 11/052,399 are specifically incorporated herein by reference in their entirety.

BACKGROUND OF THE INVENTION

1. Field of Invention

The invention relates to a device for measuring fluorescence excited by light in at least one layer containing a fluorescing material, and to the use thereof for measuring fluid materials which effect fluorescence quenching in at least one of the fluorescing layers.

Measuring methods and measuring devices customarily used to date have the disadvantage that the ratio of fluorescent light to the light required to excite the fluorescence is very low, with the result that a separation is required and, consequently, a miniaturization, which is necessary for many applications, has so far been ruled out.

Further known solutions do not achieve satisfactory separation between the exciting light and the fluorescent light.

To counter this, use has so far been made of an expensive, complicated optical design which requires many optical elements, which are also cost intensive, the result being, in particular, the appearance of problems with the miniaturization and process integration.

The known solutions also have the disadvantage that the detection of the measuring signal has proceeded relatively slowly and that furthermore, errors have occurred due to coupling drift (temperature fluctuation, mismatching, or due to modem coupling), and could be taken into account only with difficulty.

2. Description of the Related Art

DD 106 086 describes a measuring probe in which fluorescence is excited in a layer, the exciting light being directed onto the layer by a single optical fiber which surrounds, in the shape of a ring, at least one further optical fiber for fluorescent light. The fluorescent light can be measured with a detector, and the measured value thereof can be used as a measure of the content or the concentration of a material, as a consequence of fluorescence quenching. Use is made for a reference measurement of a second optical fiber which directs fluorescent light of a layer region, which is screened from the measurement medium, onto a second detector.

However, it is not possible with this solution to ensure a concrete and accurate local assignment of the detectable fluorescence intensity over the excited layer surface, something which is, however, also necessary for accurate measurements because of an imprecisely defined local excitation or a non-defined, inhomogeneous arrangement of the fluorescing material in the layer. Moreover, an absolute optical separation is necessary for a simultaneous reference measurement or further measurements for other materials.

In addition, GB 2265711 A1 describes an optical fiber sensor in which two optical fibers inclined at a specific angle to one another are to be used. In this case, one of the optical fibers serves the purpose of sending light, and the other optical fiber serves the purpose of receiving reflected light and directing it onto a suitable detector. The alignment of the two optical fibers at an angle to one another is proposed there in order to achieve enlargement of the possible detection range of reflected light, since it is possible to achieve an enlarged overlap of the light exit cone with the light entrance cone of the two optical fibers.

U.S. Pat. No. 3,992,631 describes a system and a method for carrying out fluorescence immune tests in which, inter alia, reference is made to the possibility of using different optical fibers in a bundle arrangement.

It is therefore the object of the invention to propose a device which can be of miniaturized construction and therefore be adapted flexibly to different applications and achieves a satisfactory measuring accuracy.

SUMMARY OF THE INVENTION

According to the invention, this object is achieved by means of the features of Patent Claim 1. Advantageous embodiments and developments of the invention follow in the case of the use of the features named in the dependent claims.

The device according to the invention for measuring fluorescence excited by light at least one layer containing a fluorescing material essentially comprises a measuring head in which at least one light source which emits light of wavelength(s) exciting fluorescence(s) in the layer or layers, and at least one detector which measures the intensity of the fluorescent light, are held. The light directed onto the layer(s) in order to excite the fluorescence is directed onto the fluorescing layer via at least one optical conductor. In this case, the same optical conductor can also direct the fluorescent light onto the detector. A plurality of fluorescing layers can be arranged next to one another in a fashion separated from one another locally or, if appropriate, partially overlapping, and be irradiated in each case with exciting light.

It is important for the end faces of the optical conductors of the fluorescent light at the measuring face of the measuring head to be arranged and/or aligned taking account of the numerical apertures of all the optical conductors, in order to achieve an accurate measurement of each area of the fluorescence being measured. This is necessary for an accurate local assignment of values. In doing this, it is important that the numerical apertures of the optical fibers be chosen so that the entry and/or exit cones of each optical fiber overlap with the entry and/or exit cones of the adjacent optical fibers. If this overlap is not present, some of the fluorescent and/or reflected light will not be captured, and an accurate measurement will not be obtained. A further possibility for achieving this aim consists in aligning these optical conductors with reference to one or more layer(s) containing fluorescing material(s).

For the measurement, the fluorescing layer(s) is/are arranged on the end or ends of the optical conductors or on a suitable support or a body, or make contact therewith.

Optical fibers are preferably used as the optical conductors.

There is thus, in principle, the possibility of arranging a plurality of different fluorescing layers, and using them with one or more different light sources which in each case emit light with wavelengths which excite fluorescence(s). It is thereby possible, with the aid of only one measurement using a single measuring head having at least one fluorescing optical fiber for each of said plurality of different fluorescing layers, to detect a plurality of different fluid materials, which effect fluorescence quenching in the different layers.

However, the invention can also be developed for the use of a plurality of optical fibers, which direct different types of light to different detectors arranged separately from one another.

Thus, for example, the light of a light source can be directed onto a fluorescing layer by a first optical fiber, from there the fluorescent light can be directed by a second optical fiber onto a detector arranged in the measuring head, and, for the purpose of obtaining a reference signal, exciting light reflected in the layer can be directed onto a second detector by a third optical fiber. For each additional type of fluorescing material present, for example, a second fluorescing dye, an additional fluorescing optical fiber, may be provided.

In this case, the fluorescing layer or a plurality of fluorescing layers which are preferably applied to a substrate serving as support can simply be plugged onto the measuring head using a cap or an exchangeable support, thus rendering a simple exchange possible. In this case, it is particularly advantageous when a coupling medium is present between the substrate, to which the fluorescing layer(s) is/are applied, and the ends of the optical fibers, in order to reduce light losses.

It is favorable for various applications when at least a part of the measuring head, and in this case at least the part which holds the optical fibers, which is directed in the direction of the fluorescing layer(s), is of flexible construction, or the upper part of the measuring head is at least partially bent.

In order to improve the optical properties of the device according to the invention, it is advantageous for a filter and/or a launching optical system to be arranged between the light source or sources and the respectively assigned optical fibers, in order, on the one hand, to avoid light losses and, on the other hand, to delimit the wavelength region of the light which is directed onto the respective fluorescing layer, so that the measuring errors can be further reduced. It is particularly favorable that the filters can be exchanged for others which are suitable for other wavelengths, that is to say other fluorescing materials, and consequently also other materials to be detected.

A corresponding arrangement of coupling-out optical systems and/or filters upstream of the various detectors acts in the same way.

In the device according to the invention, however, it is also possible to make use of a bundle of a plurality of optical fibers, it being possible to arrange the individual optical fibers in the bundle differently in order to be able to detect optimum measuring signals of fluorescent light, and reflected light of the light source(s) moreover measuring errors can be minimized. The arrangement of the individual optical fibers in the bundle can be performed in this case in the shape of a ring, in one variant, and in the shape of concentric rings in a second variant.

In the case of an arrangement in the shape of a ring, it is possible to arrange next to one another in an alternating fashion, in an outer ring, optical fibers which, on the one hand, direct exciting light onto the fluorescing layer and, on the other hand, direct light reflected there as reference signal onto a detector. It is then possible to arrange internal thereto optical fibers which direct fluorescent light onto at least one detector in the measuring head. An additional optical fiber which likewise directs exciting light onto the fluorescing layer can then be arranged at the centre of the ring.

In another arrangement of the individual optical fibers, it is favorable to arrange an optical fiber through which exciting light is directed onto the fluorescing layer, and to arrange next to one another, in an alternating arrangement, optical fibers with which reference light and fluorescent light are directed onto detectors.

The arrangement of the respective optical fibers for the various types of light can, however, also be selected taking account of the arrangement of different fluorescing layers, it being possible, for example, to select an arrangement of the optical fibers in the shape of a circular arc when the fluorescing layers are constructed as circular arcs.

In another embodiment of the device according to the invention, the individual optical fibers are not, however, arranged in parallel but, at least in their end regions, that is to say in the direction of the fluorescing layer(s), are inclined at specific angles to one another, so that, for example, fluorescence-exciting light is directed at a specific angle, which is not equal to 90°, onto the fluorescing layer, and there is aligned at a second correspondingly aligned angle at least one optical fiber by which the reflected reference light can enter and be directed onto a detector. A third optical fiber can then preferably be arranged orthogonally relative to the fluorescing layer through which the fluorescent light reaches the corresponding detector.

In all these cases, however, it is favorable to arrange and/or align the optical fibers such that for the purpose of launching and coupling out exciting and fluorescent light their end faces are arranged, taking account of their numerical apertures, so that the entry and or exit cones of the optical fibers overlap.

It is favorable for specific applications of the device according to the invention when, at least in the upper measuring head region, a heater is present which can prevent condensation of, for example, water on the fluorescing layer (s). Moreover, it is favorable to use at least one temperature sensor and a corresponding controller or regulator to manipulate the heater in accordance with the ambient conditions, that is to say the ambient temperature and the atmospheric humidity, and thereby to be able to set different perceivable temperatures in the region of the fluorescing layer(s) and/or in the upper measuring head region. The heater can in this case be arranged in the upper measuring head region, but it is also possible to arrange appropriate heating elements in the immediate vicinity of the fluorescing layer(s). One possibility for this is to fit the heater on the substrate to which the fluorescing layer(s) is/are applied.

The device according to the invention can further be improved when the lower region of the measuring head is constructed in a thermally insulated fashion with respect to the upper heated measuring head region.

It can be favorable for various applications to construct the upper measuring head region not only in a flexible fashion but also in a tapering fashion, solely or in conjunction with a flexible design, it being possible to taper virtually to the diameter of the optical fibers.

Depending on the actual design of a measuring device according to the invention, it is possible to detect at least one fluid material which affects a specific quantifiable measure of fluorescence quenching in the fluorescing layer. It is also possible to detect different materials with different fluorescing layers which are arranged next to one another. However, it is also possible, in principle, to detect a plurality of materials by directing light of different wavelengths onto only one fluorescing layer and carrying out the detection in terms of wavelength resolution.

Despite an at least partially integrated electronic evaluation system, the device according to the invention must be of small and flexible construction so that the most varied applications are possible. In particular, the slim and, if appropriate, flexible construction of the upper measuring head region has the positive effect that alignment relative to the measuring location or to the fluorescing layer(s) is possible in a simple way.

A further advantage consists in that the optical fibers can be used without rigid connections, such as optical connectors, with the result that an exchange is possible although the optical fibers are held fixed and therefore can no longer be moved, it thereby being possible to avoid modal noise.

If a plurality of optical fibers are used as a bundle, varied arrangements at the end of the measuring head in the direction of the fluorescing layer(s) can ensure optimum measuring conditions and reduce the component of scattered light as well as greatly minimize cross talking of exciting light, and it is also possible in this case to detect a reference signal.

The spatial separation and additional thermal insulation of the upper measuring head region can optimize the temperature control in the region of the fluorescing layer(s) with reference to energy consumption, and unnecessary heating of the lower region of the measuring head is prevented.

Further advantages of the invention are the better and more effective illumination of the fluorescing layer(s), and less influence from extraneous and scattered light.

The invention can take account of a plurality of material concentrations by means of different fluorescent dyes and/or reference signals. It is possible for such layers to be selectively excited and correspondingly detected.

The temperature control or heating can be carried out only in the immediate vicinity of the layers.

There is no need for any external optical connectors which could lead to coupling problems.

Miniaturization, a lower mass and, in addition, flexible access to the measuring medium are possible by optical separation of measuring tip and the detection and evaluation of measured values.

The device according to the invention is not only capable of flexible construction, but is also cost-effective to produce and operate, since some parts can also be replaced cost-effectively by being exchanged.

BRIEF DESCRIPTION OF THE DRAWINGS

The invention is to be described in more detail below using exemplary embodiments.

DETAILED DESCRIPTION OF THE PREFERRED EMBODIMENT

Figure 1:
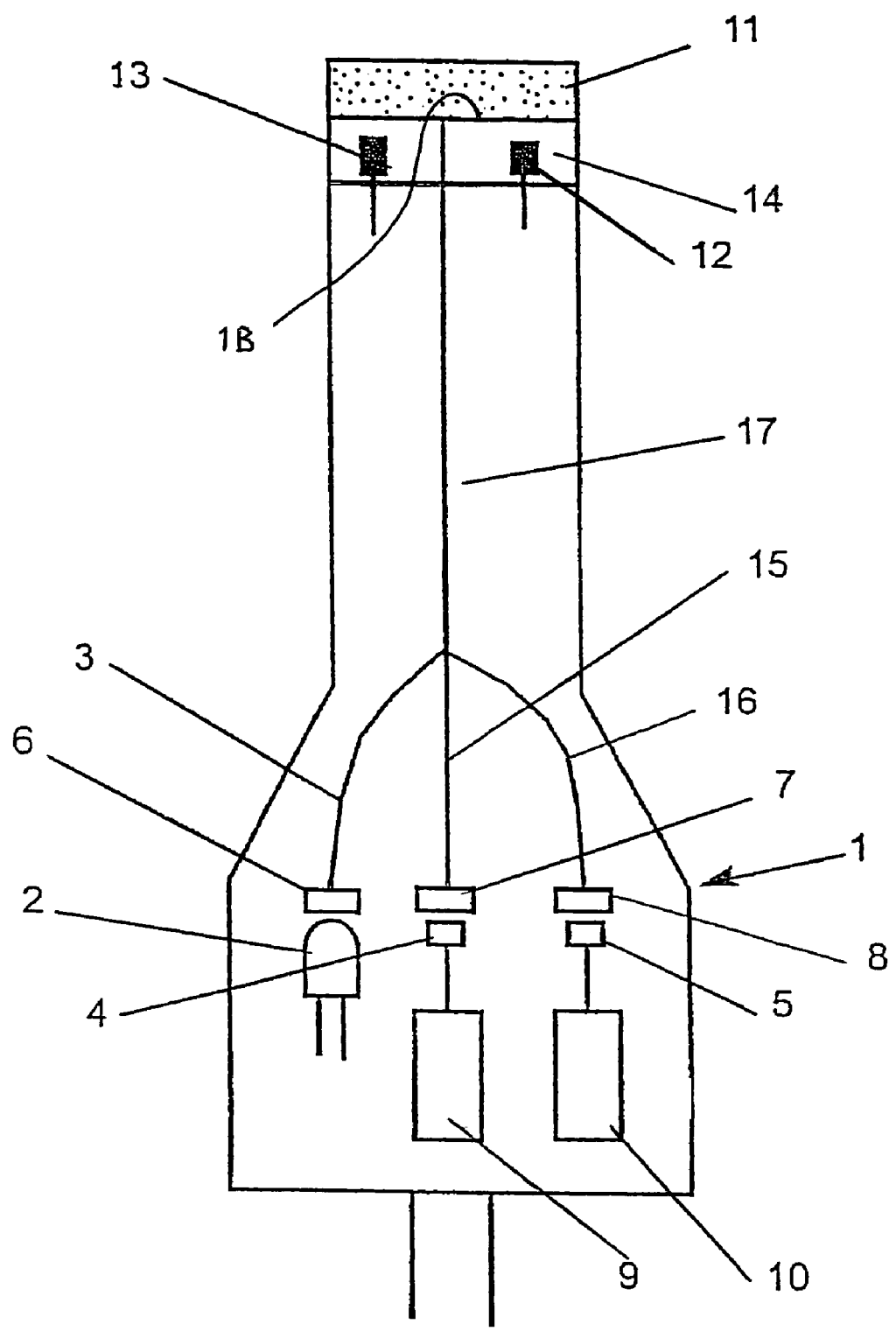
FIG. 1 shows the diagrammatic design of a first example of a device according to the invention.

The diagrammatic design of a first exemplary embodiment of a device according to the invention is represented in FIG. 1. There is shown a measuring head 1, having a face 1B on a metal tip 14 to which a fluorescing layer 11 is applied. The fluorescing layer 111 may also be applied to a support 30 (FIGS. 4-15) which is in contact with the face 1B, thus placing the fluorescing layer 11 in optical contact with the face 1B.

In this case, there is held in the closed measuring head 1 at least one light source 2 from which exciting light is directed onto a fluorescing layer 11 via a filter 6, which is preferably also an exchangeable band pass filter, by the first optical fiber 3, which is guided through the upper measuring head region 17. Fluorescent light from the fluorescing layer 11 passes through a second optical fiber 15 via an edge filter 7, possibly likewise exchangeable, onto a detector 4 with which the intensity of the fluorescent light can be measured, and the detector 4 is connected to an electronic evaluation system 9.

Reflected light then passes as a reference signal through a third optical fiber 16, likewise via a filter 8, which can, again, be exchangeable, onto a second detector 5, which is connected to a second electronic system 10.

In this case, the exchange of the filters 6, 8 is advantageously possible from outside via openings with a lock. Thus, when the measuring head 1 is finished measuring one type of fluorescence, and is to be used in another application, the filters 6,8 can be removed from measuring head 1, and replaced with whatever filters are needed for the new application, all with a minimum of downtime and expense.

A heater 12, which may be mounted in a metal tip 14 in order to improve the thermal conduction, is provided in the uppermost region of the upper measuring head region 17. Likewise held in the metal tip for the purpose of controlling or regulating the heater 12 is a temperature sensor 13 whose measuring signal is led to an electronic control system which then influences the heat output.

Two lines at the lower part of the measuring head 1 indicate connections to an electronic evaluation system which can further process the preprocessed signals from the electronic systems 9 and 10, and 5 display and output them.

Of course, the number of the light sources 2 of the detectors 4 and 5 can be appropriately increased.

Figure 2:
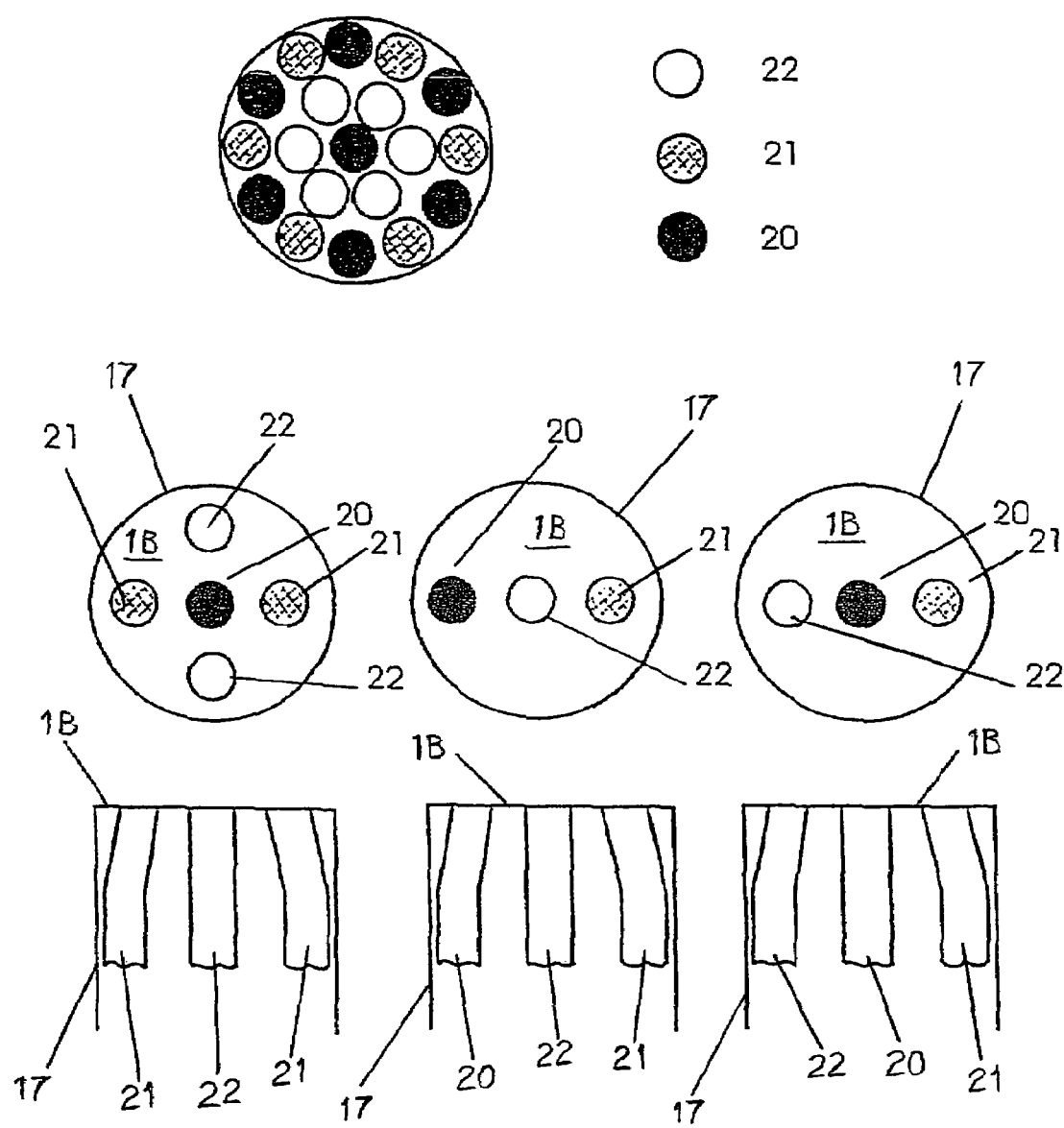
FIGS. 2, 2a and 2b show various arrangements of optical fiber bundles on the upper measuring head.
Figure 2A:
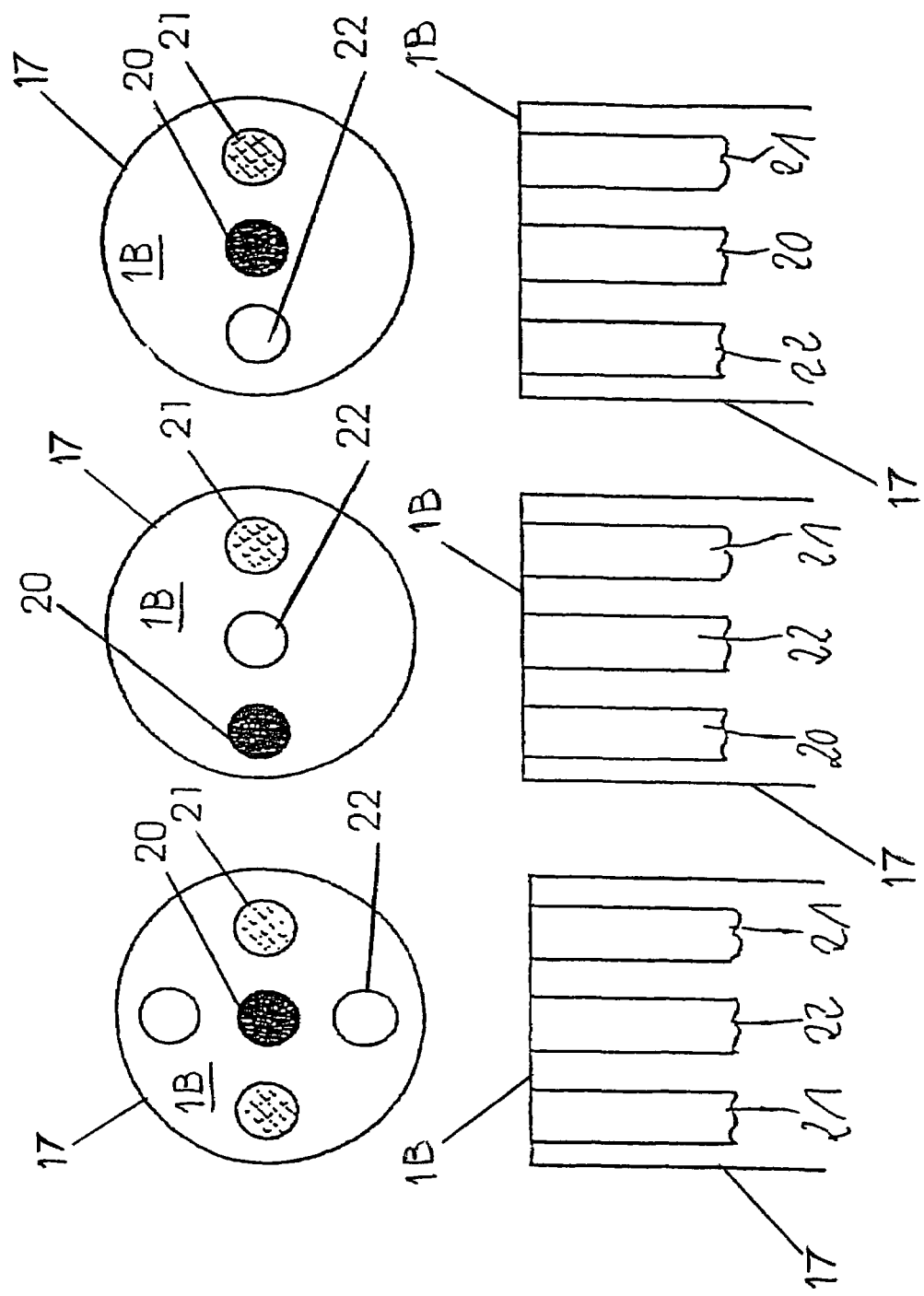
Figure 2B:
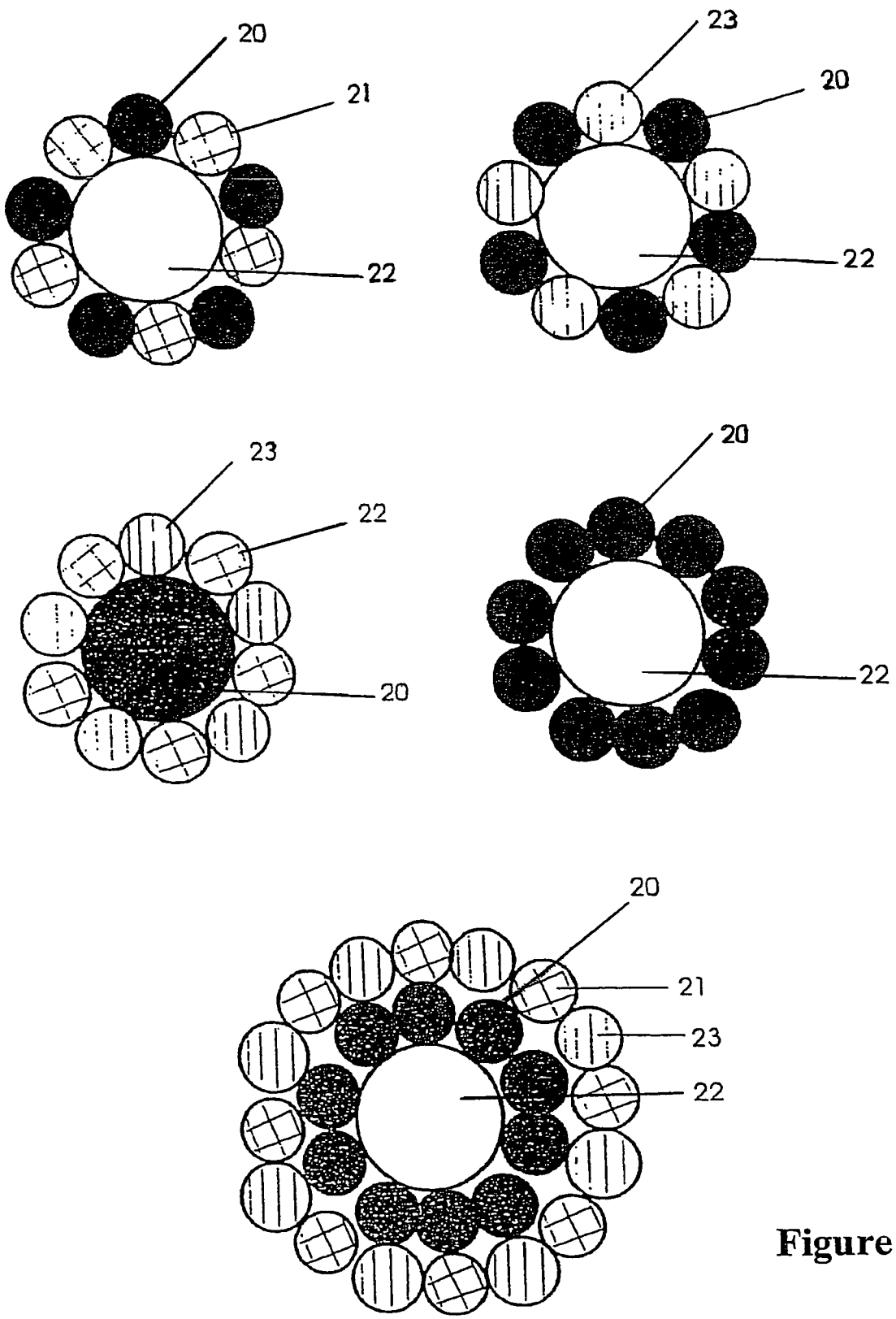

Different variants for possible arrangements of different optical fibers are then represented in FIGS. 2, 2a and 2b. Referring first to FIG. 2, the upper representation in FIG. 2 shows a bundle of different optical fibers, the excitation optical fibers 20 directing light of the light source 2 onto the fluorescing layer. The reflected light optical fibers 21 direct the light reflected at the fluorescing layer as a reference signal onto the detector 5, and the fluorescing light optical fibers 22 direct fluorescent light from the fluorescing layer or layers onto one or more detector(s) 4.

Shown in the lower left hand representation of FIG. 2 is face 1B of measuring head 1 at the upper measuring head region 17. In this arrangement of optical fibers, an excitation optical fiber 20 is centrally located with its' longitudinal axis orthogonal to the face 1B. Laterally aligned with excitation fiber 20 are a pair of reflected light fibers 21, one on each side of the excitation fiber 20. Arranged orthogonally to the axis of the reflected light fibers 21, with respect to the face 1B, are a pair of fluorescing light optical fibers 22. In this arrangement at least the reflected light fibers are bent at their ends near the face 1B, Thus, the axis of the reflected light fibers at the face 1B are not parallel to the axis of the excitation light fiber 20.

In the lower middle representation of FIG. 2 is shown an arrangement of fibers where the axis of both the excitation light fiber 20, and the reflected light fiber 21, are not parallel to the axis of the fluorescing light fiber 22.

In the lower right representation of FIG. 2 is shown an arrangement of fibers where the axis of both the excitation light fiber 21 and the fluorescing light fiber 22, are not parallel to the axis of the excitation light fiber 20.

In all the representations of FIG. 2, the numbers of the excitation light fiber 20, the reflected light fiber 21, and the fluorescing light fiber 22 can be increased at will.

In the lower representations of FIG. 2, furthermore, the arrangement of the different optical fibers 20, 21 and 22 in the upper measuring head region 17 is represented in preferred form. In this case, different optical fibers, arranged in the outer region, in particular, are constructed in an angled fashion so that it is possible to achieve an improved illumination of the fluorescing layer, and a reduction in the influence of extraneous light and scattered light.

The examples represented in FIG. 2 are not, however, limited to a design of a measuring head, according to the invention, in which only one fluorescing layer is used. When a plurality of different fluorescing layers are used on the measuring head according to the invention, an arrangement of the different optical fibers required for the measurement of the multiple fluorescing layers can be performed in a simple way, with the result that optimum conditions can be obtained in each case for the various fluorescence and reference signals.

Referring to the upper left representation of FIG. 2b, in some applications it is preferred to have a respectively very large single fluorescing light fiber 22 surrounded by a ring of alternating exciting light fibers 20 and reflected light fibers 21.

Referring to the upper right representation of FIG. 2b, there is shown an arrangement of fibers, which is useful when two different types of fluorescing materials, such as two fluorescing dyes, are being measured. Since two different types of fluorescing materials are being measured, two separate and different fluorescing fibers are needed. In this arrangement, a relatively large first fluorescing fiber 22 is centrally located. First fluorescing fiber 22 is surrounded by a ring of alternating exciting light fibers 20 and second fluorescing light fibers 23.

In each case, the optical fibers 22 can, however, be arranged and/or aligned such that, even taking account of their own numerical apertures and those of the optical fibers 20 for exciting light, locally defined regions can be detected in the layer or layers. Arrangements are possible with one detector having two light sources, or one light source having two detectors, depending on the application.

It is also preferable to have arrangements which are adapted to measure two or more separate areas or channels of the fluorescing layer or layers. In this case, it is necessary to have either a single light source with separate bundles of fibers arranged in pairs, or multiple light sources, isolated from each other, but each associated with specific pairs of bundles of fibers. Such arrangements are useful to take into account bleaching of the fluorescing layer, use of different dyes, or dyes having different sensitivities.

Figure 3:
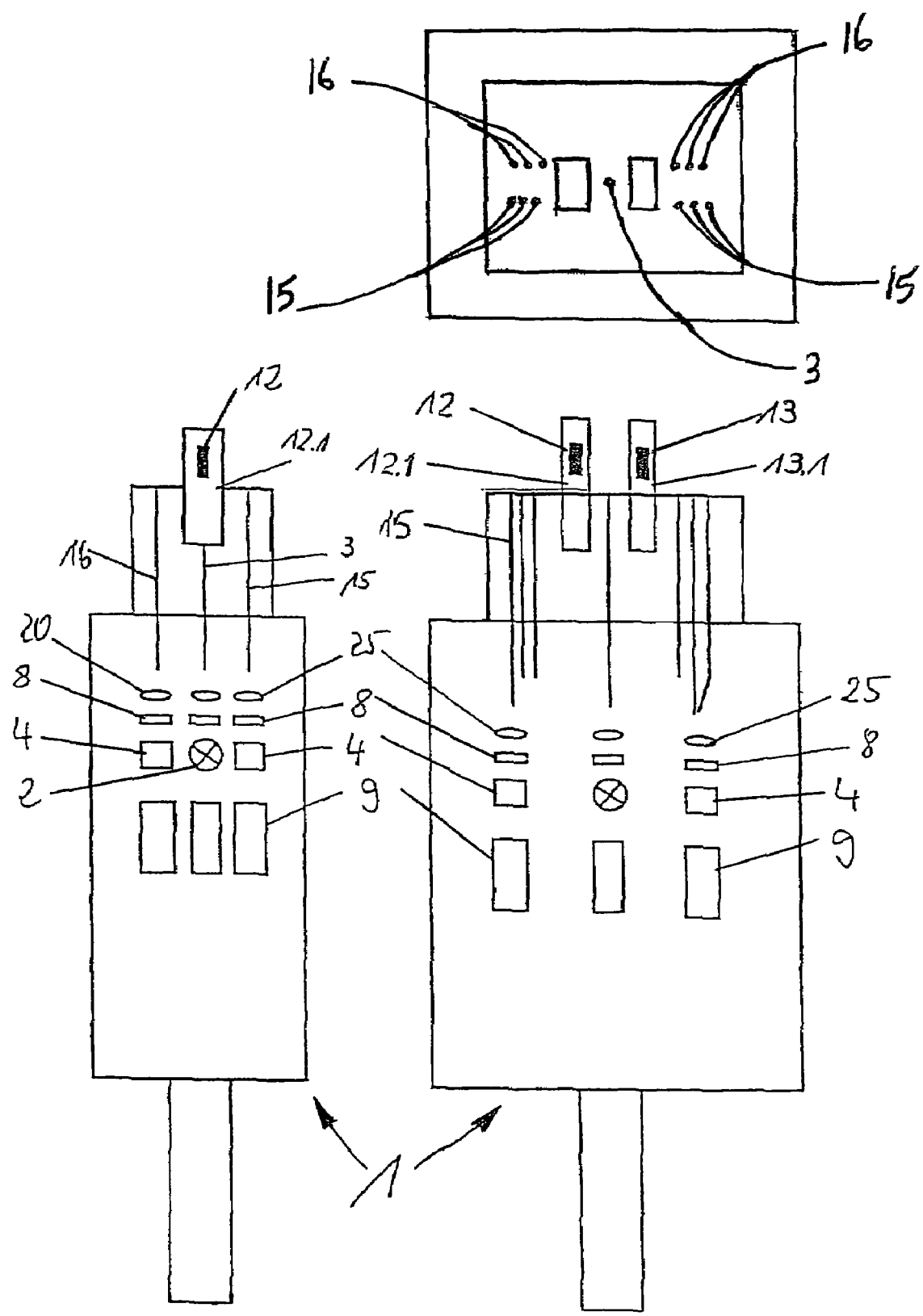
FIGS. 3, 3a and 3b show three examples of a measuring head according to the invention.

Referring now to FIG. 3, a second example of a measuring head 1 according to the invention is shown wherein measuring head 1 is shown having a smaller width in relation to its length, and therefore, in particular, offers more favorable preconditions for measurement in flowing media than is the case with, for example, circular or square shapes, since the flow conditions, and consequently also the measurement result, can be negatively influenced by, for example, turbulence which is produced, higher flow rates or pressure rises.

Exchangeable supports, of which a few examples are represented in FIGS. 4 to 15 still to be described below, can then be mounted on such a measuring head 1.

As is also to be seen in FIG. 3, optical fibers 15 and 16 can be arranged in row arrangements opposite one another in pairs, the rows being aligned parallel to the longitudinal axis of such a measuring head. Referring to the top or plan view of the measuring head 1, shown at the top right of FIG. 3, a first pair of rows of optical fibers (15,16) is shown proximate the left end of the measuring head 1, and a second pair of rows of optical fibers (15,16) is shown proximate the right end of the measuring head 1.

It is also possible in this case to arrange in one row exclusively optical fibers 3 for exciting light, and in the opposite row exclusively optical fibers 15, 16 for fluorescent light, or at least in one row an alternating arrangement of optical fibers 3 for exciting light and optical fibers 15, 16 for fluorescent light.

Accommodated once again in the measuring head 1 are the light sources 2, preferably exchangeable filters 6 and 8, launching and coupling-out optical systems 25, detectors 4 and the corresponding electronic evaluation and control system 9.

Also represented in FIG. 3 are temperature sensors 13 and heating elements 12 which project from the upper socket of the measuring head 1 in the form of a pin or in another suitable form, so that they can be positioned and fixed in a self-closed fashion in connection with correspondingly constructed holding bores in the supports 30 or bodies 40 (still to be described).

The supports 30 or bodies 40 can be mounted on the otherwise planar surface of the socket by means of an optical cement.

Figure 3A:
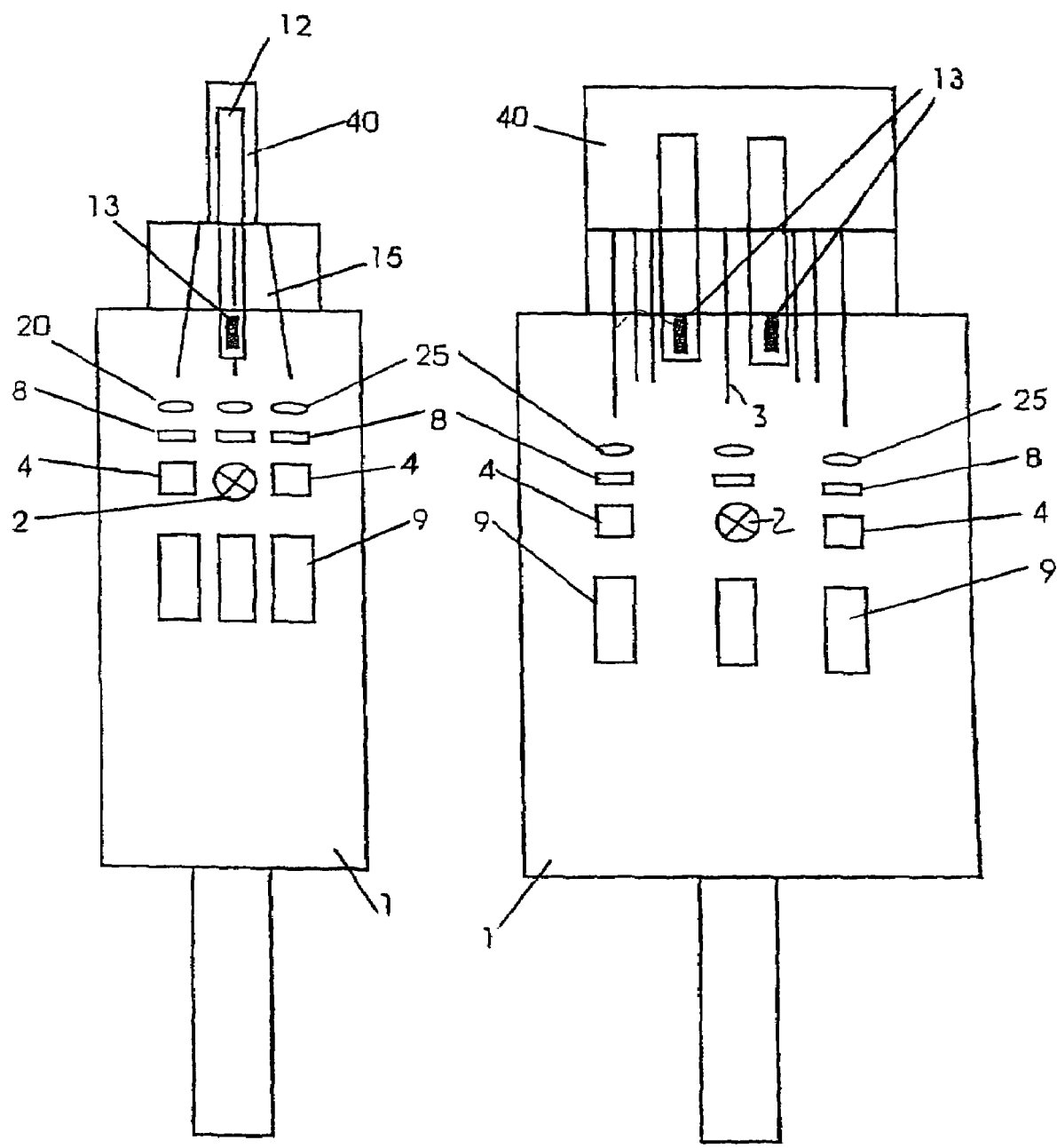
Figure 16:
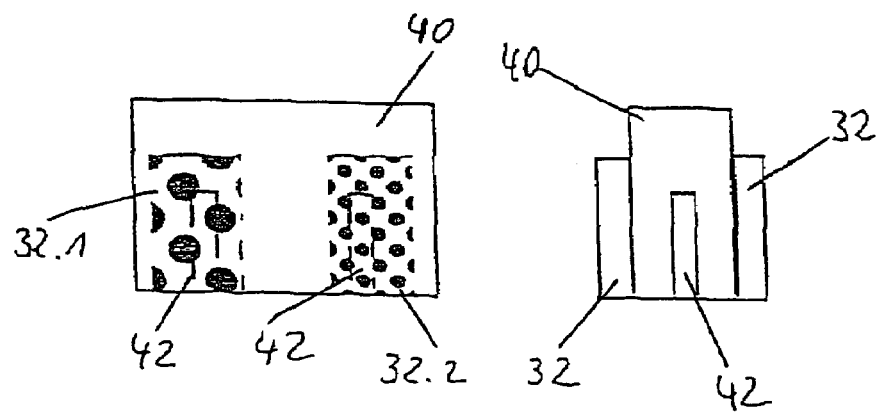
FIG. 16 shows a body which can be mounted on a measuring head.

Referring now to FIG. 3A, measuring head 1 with a mounted body 40 in accordance with FIG. 16 is shown. Similarly to that shown in FIG. 3, and referring to the top or plan view of the measuring head 1, shown at the top right of FIG. 3A, a first pair of rows of optical fibers (15,16) is again shown proximate the left end of the measuring head 1, and a second pair of rows of optical fibers (15,16) is shown proximate the right end of the measuring head 1.

Figure 3B:
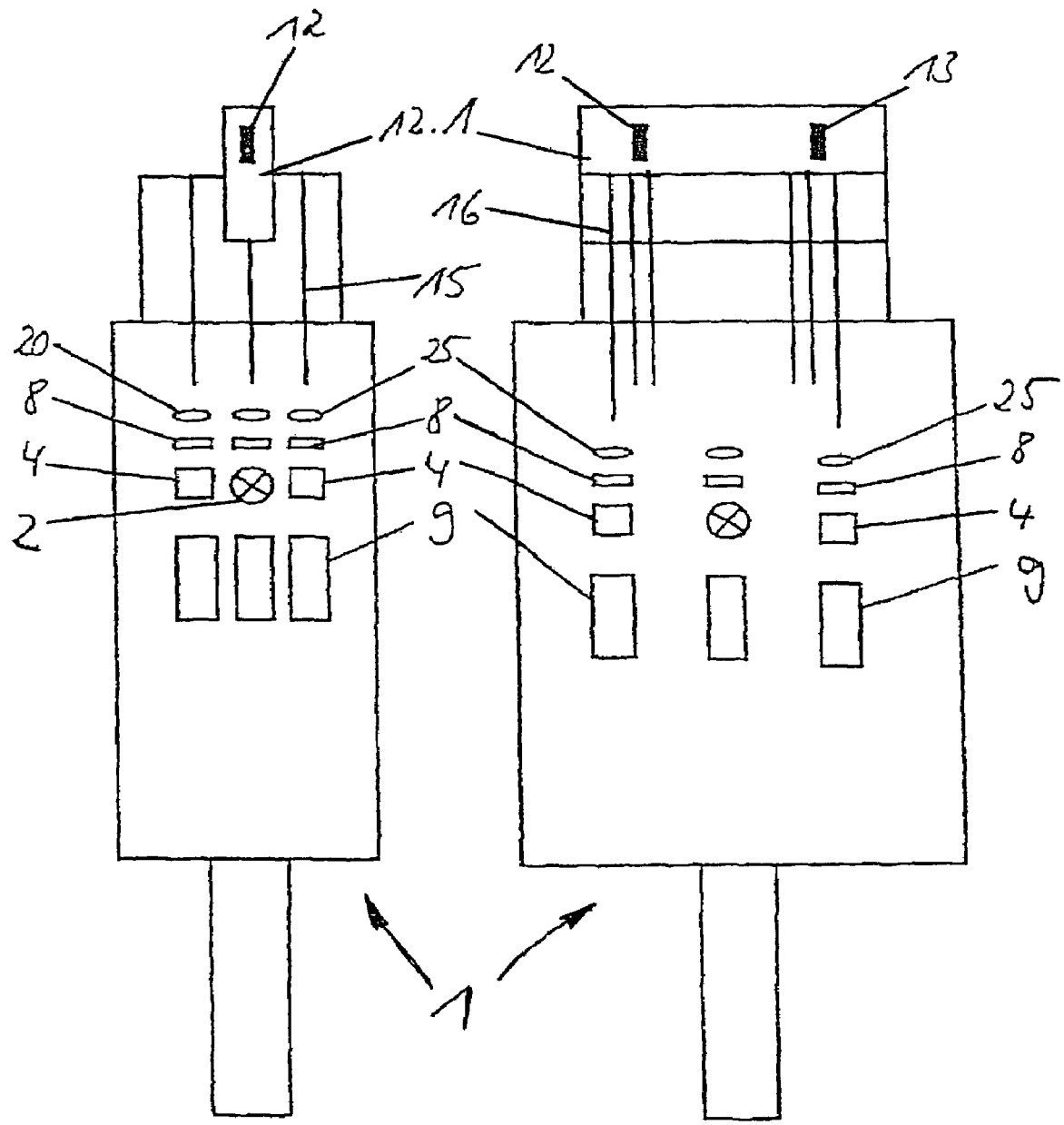

FIG. 3b shows an example of a measuring head 1 on which, again, a support 30 or body 40 can be mounted. The single or a plurality of heating element(s) 12 can be surrounded by a material 12.1 having good thermal conduction. If desired, a first pair of rows of optical fibers (15,16) may be arranged proximate the left end of the measuring head 1, and a second pair of rows of optical fibers (15,16) may be arranged proximate the right end of the measuring head 1. Those skilled in the art will appreciate that a wide variety of arrangements of optical fibers (3,15,16) supports 30 or bodies 40 can be used, and are well within the scope of the present invention.

Figure 3C:
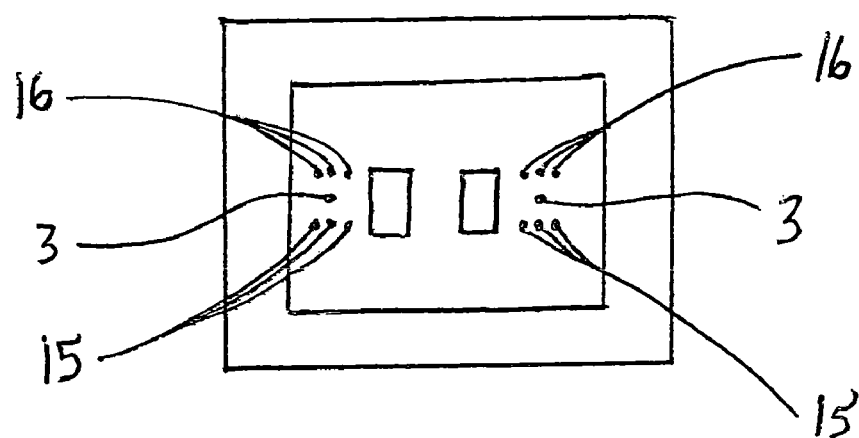
FIG. 3c shows a modification of the measuring head shown in the upper representation of FIG. 3, wherein each pair of optical conductors is associated with its own light source which is not seen by the other light source, and may emit a different light.

With reference to FIG. 3c, there is shown an arrangement wherein two channels or areas of a fluorescing layer can be easily measured. There is shown two light sources 3, each of which cannot be seen by the other, and each of which has rows of second optical fibers 15, and third optical fibers 16 arranged opposite each other in pairs. It can be understood that there could be three, or more, such arrangements on a single measuring head 1 because of the miniaturization achieved by the present invention. Each arrangement would measure a different area of a fluorescing layer to permit accurate local assignment of value to the fluorescing layer.

Figure 4:
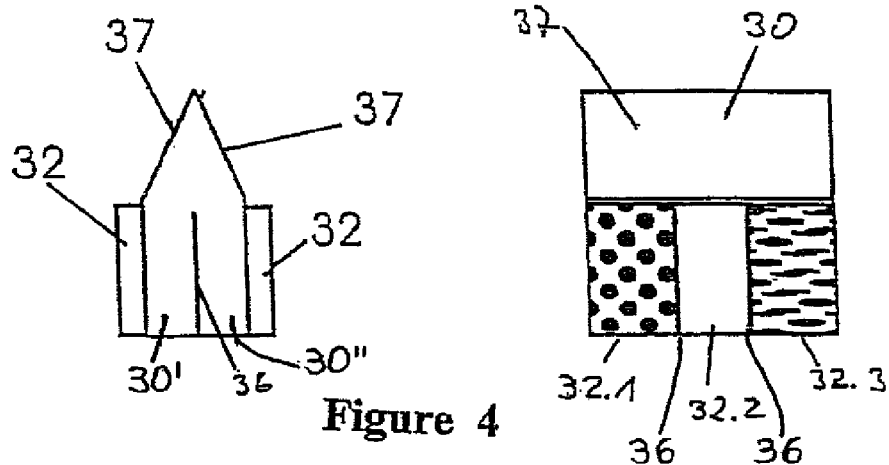
FIG. 4 shows a first example of a support which can be mounted on a measuring head, in two views.

Represented in two different views in FIG. 4 is a first example of a support 30 which, as represented in FIG. 3, can be mounted on a measuring head 1, and is made from an optically transparent material.

It is to be noted here that, as also holds for the following pictorial representations in FIGS. 5 to 13, the proportions do not correspond to the actual ones, rather, to simplify and improve comprehension, the width is represented to be substantially larger than is the case in a practical design, and in that for use in flowing fluid media the width of such a support 30 is substantially smaller in relation to its length, with the result that the flow resistance is kept correspondingly low.

The support 30 in accordance with FIG. 4 comprises two limbs 30', 30" which are optically separated from one another at least partially by an interposed, preferably reflecting layer 36.

In this example, layers 32 containing fluorescing materials are applied to both outer sides of the support 30, and the remaining outer surfaces 37 are likewise constructed or coated to be reflective.

The exciting light is now irradiated via optical fibers 3 into at least one of the two end faces of the limbs 30', 30" into the transparent support 30, and the fluorescence is excited there in the layers 32 by multiple reflection. A portion of the fluorescent light is irradiated again onto the support 30 and, by reflection at the outer surfaces of the support 30, directed onto optical fibers 15, 16 for fluorescent light by the lower end faces of one or both limbs 30', 30", and the intensity of the fluorescent light is detected by detectors 4 and, consequently, the material concentration can be measured as a consequence of fluorescence quenching.

Also to be seen in the left-hand representation of FIG. 4 is the fact that the upper bounding surfaces of the support 30 are constructed inclined at an angle to one another, the angle being selected such that optimum reflection conditions can be achieved in accordance with the wavelengths used.

Represented in the right-hand representation of FIG. 4 is a view orthogonal to the longitudinal axis of such a support 30, from which it may be seen that a plurality of regions can be separated optically from one another (also possible in the following examples) by, for example, reflecting layers 36, and different layers 32.1, 32.2 and 32.3 are applied or constructed in the regions. Given these different layers 32.1 to 32.3, it is possible to use a measuring head 1 according to the invention to determine a plurality of material concentrations simultaneously and/or to carry out at least one reference measurement in one of these regions. The same reference numerals are used for identical elements in the following figures.

Figure 5:
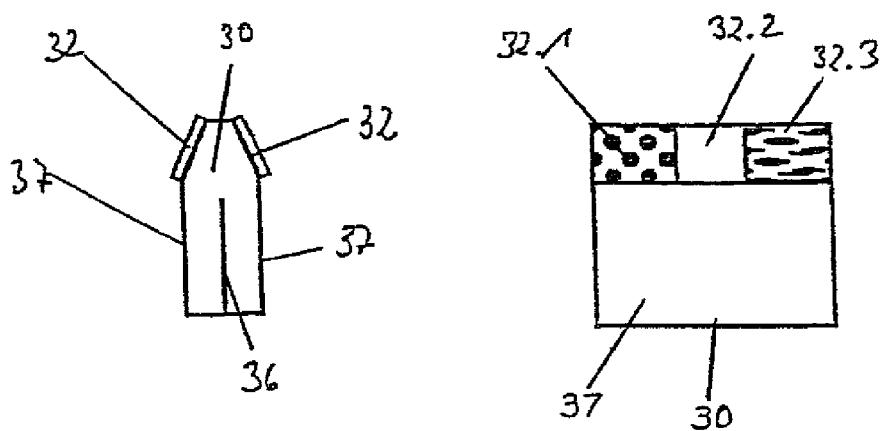
FIG. 5 shows a second example of a support which can be mounted on a measuring head, in two views.

A further variant of a support 30 is represented in FIG. 5, this variant differing from those previously described only in the outer contour.

Figure 6:
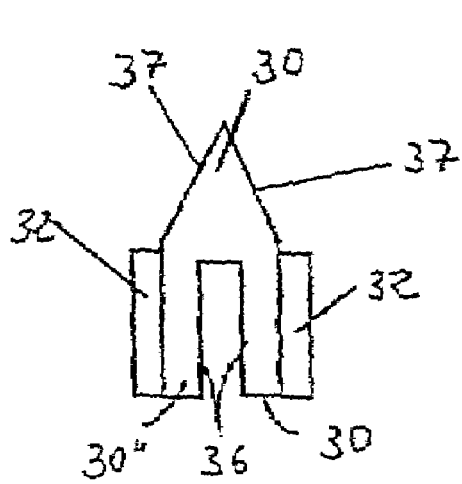
FIG. 6 shows a third example of a support which can be mounted on a measuring head, in two views.
Figure 6:
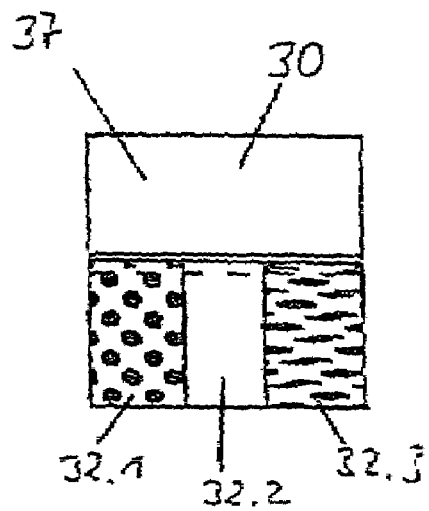

The example, represented in FIG. 6 likewise in two views, of a support 30 which can be mounted on a measuring head 1 according to the invention corresponds essentially to parts of the support 30 already mentioned in the description of FIG. 4.

The only point is that a cavity reaching over the entire length of the support 30, or one or more cutouts, whose surfaces are also provided with a reflecting coating 36 is/are constructed between the limbs 30' and 30".

A self-closing fastening on the measuring head 1 can be achieved with this cavity or the cutout(s).

Constructed for this purpose on the surface of the measuring head 1 is an appropriate longitudinal web which can engage in a self-closed fashion in the cavity constructed in the support 30, and can hold it correspondingly.

If one or more cutouts are constructed in the support 30, the correspondingly shaped and contoured heating elements 12 and temperature sensors 13, or other, for example, pin-shaped elements without a further function, can, constructed exclusively for fastening such a support 30 on the measuring head 1, be inserted into the cutouts or cavities in a self-closed fashion and be held there fastened appropriately.

Figure 7:
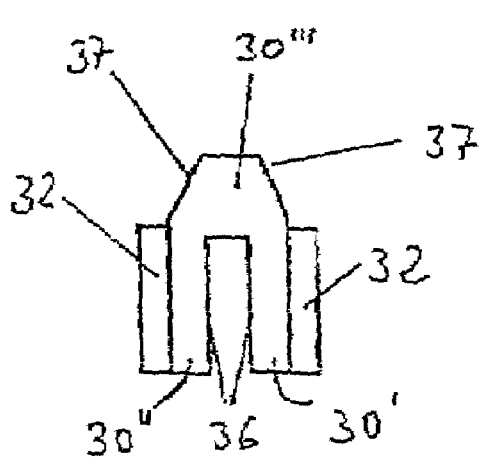
FIG. 7 shows a fourth example of a support which can be mounted on a measuring head, in two views.
Figure 7:
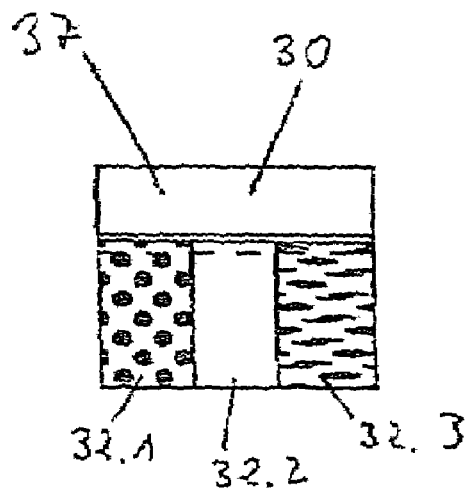

The support 30 likewise represented in two views in FIG. 7 differs from the support 30 shown in FIG. 6 once again only in the web-like flattening in the upper region.

Figure 8:
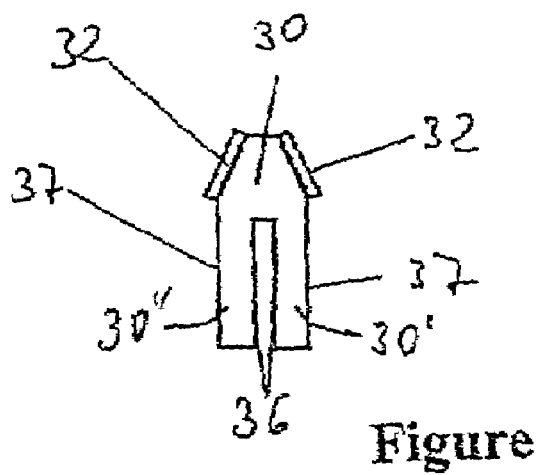
FIG. 8 shows a fifth example of a support which can be mounted on a measuring head, in two views.
Figure 8:
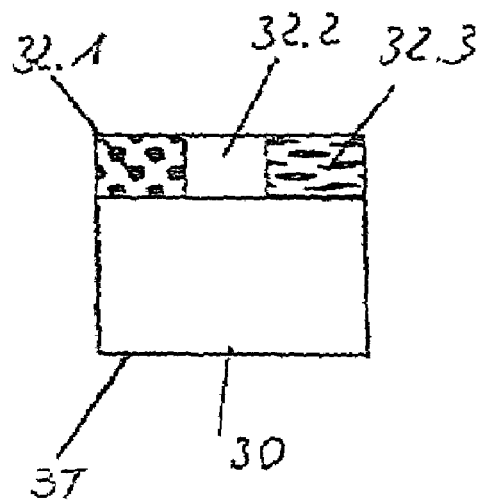

In the support 30 represented in FIG. 8, the layers 32 containing fluorescing materials are applied in the inclined upper region, with the result that they are not aligned parallel to one another, but are inclined relative to one another.

Figure 9:
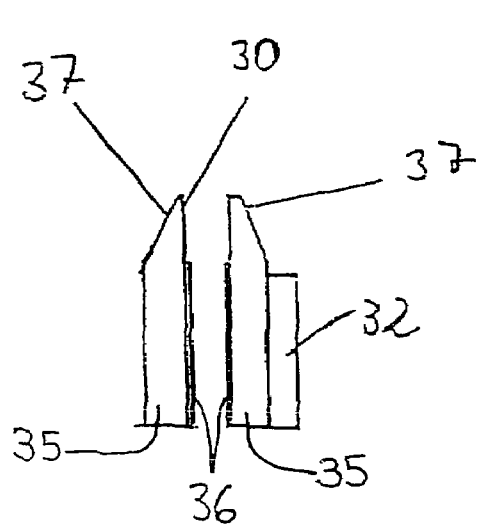
FIG. 9 shows a support with a symmetrically constructed planar optical conductor.
Figure 9:
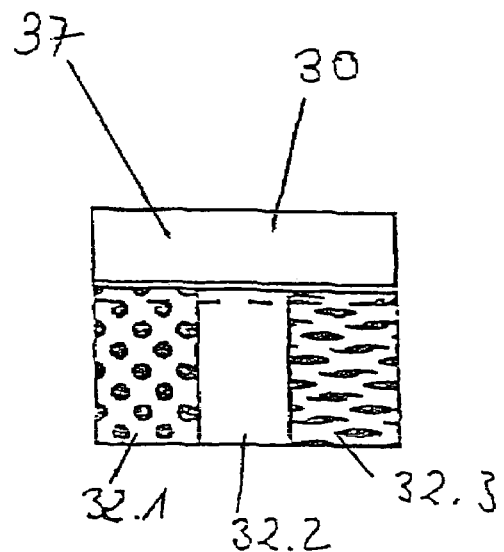

A particular design has been selected in the example of a support 30 represented in FIG. 9. Use is made in this case only of a support 30 to which layer(s) 32.1 to 32.3 containing one or more fluorescing materials are applied, and, at a spacing there from, an otherwise symmetrically constructed planar optical conductor 35 which both have, above the layer(s) 32 containing fluorescing materials, a surface which is inclined at an angle and at which both the exciting light and the fluorescent light are reflected. In this example, exciting light is launched exclusively into the lower end face of the support 30 and reflected therein, so that fluorescence is excited in the layer(s) 32. Since the opposite surfaces of the support 30 and of the planar optical conductor 35 are constructed or coated in a reflecting fashion only in the lower part, at least a portion of the fluorescent light can pass by reflection at the inclined surface of the support 30 into the planar optical conductor 35 and be directed from the lower end face thereof via the appropriately arranged optical fibers onto the detectors for the purpose of measuring the fluorescence intensity. However, instead of the reflecting layers 36, it is also possible to introduce a less strongly refracting medium into the interspaces in a fashion producing the same effect, this state of affairs also being valid for the examples according to FIGS. 6 to 8.

Moreover, instead of the planar optical 35 conductor 35, it is also possible to use a second support 30, so that a symmetrical arrangement can be achieved, in which case it is then also possible thereby to apply different layers 32.

Figure 10:
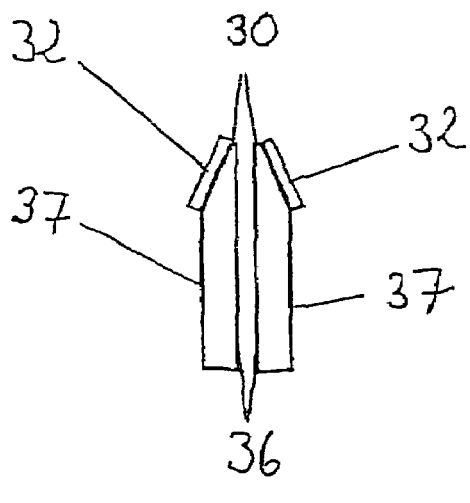
FIG. 10 shows two symmetrically arranged supports.
Figure 10:
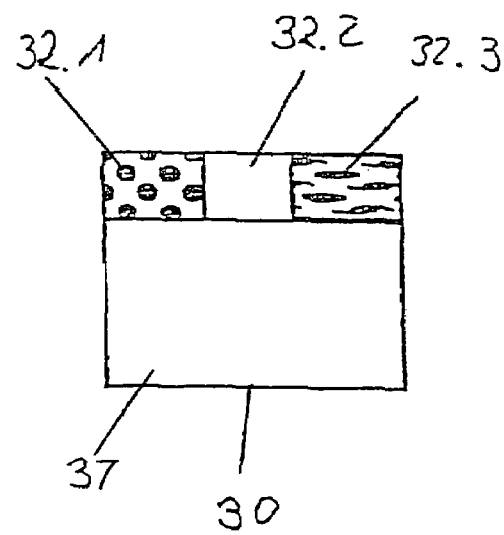

In the example represented in FIG. 10, by contrast, for example in accordance with FIG. 9, the layers 32 containing fluorescing materials are constructed or applied in the upper, inclined region of the supports 30.

In the supports 30 represented in FIG. 4 to FIG. 15, the layers 32 containing fluorescing materials can be applied directly to the corresponding surfaces of the supports 30. In another variant, however, the layers 32 containing fluorescing materials can be applied in advance to a preferably plate-shaped transparent substrate and be fastened subsequently thereto on the respective support 30 at the respective location, it being possible for this purpose to make use of mechanically acting self-closed and/or force-closed connections alone or in conjunction with an optically suitable binding agent, or of such a binding agent alone.

Figure 11:
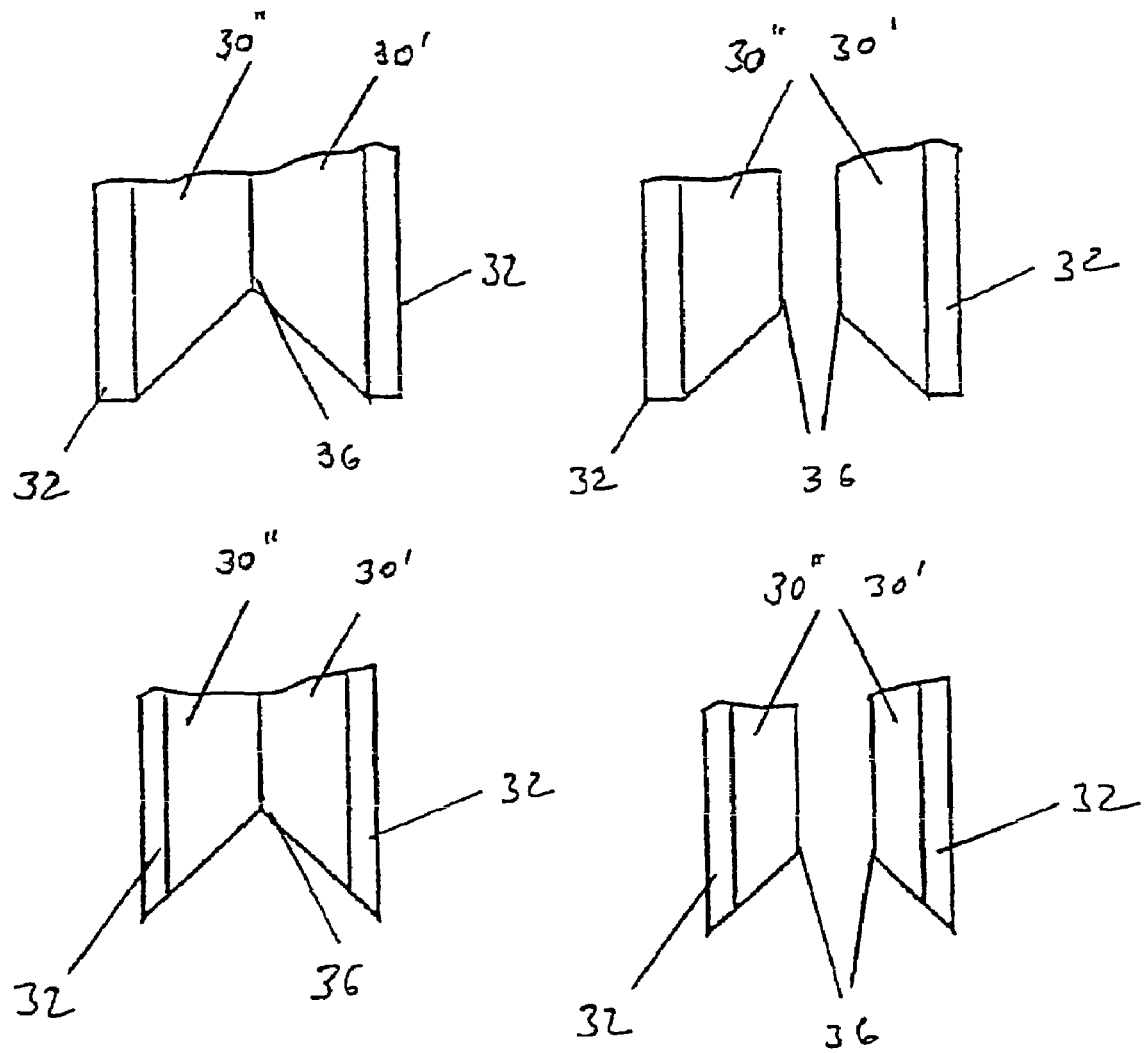
FIG. 11 shows examples for launching light into, and coupling it out of end faces of, supports which can be mounted on a measuring head.

FIG. 11 represents possible variants of the construction of end faces of the supports 30 or of the planar optical conductors 35 into which or from which the exciting light or the fluorescent light can respectively be launched or coupled out, these end faces being correspondingly inclined in all these examples such that the reflection in the limbs 30', 30" of the supports 30 can be optimized, on the one hand, for the excitation of the fluorescence and, on the other hand, for the alignment of the fluorescent light to be measured.

In these cases, the upper part of the measuring head 1, on which such a support 30 is to be mounted, must be of complementary shape in order to avoid optical losses. The same also applies to the supports 30 of the examples according to FIGS. 14 and 15.

Figure 12:
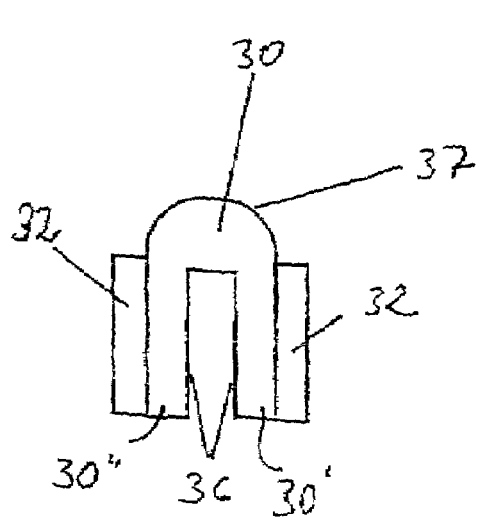
FIG. 12 shows a sixth example of a support which can be mounted on a measuring head, in two views.
Figure 12:
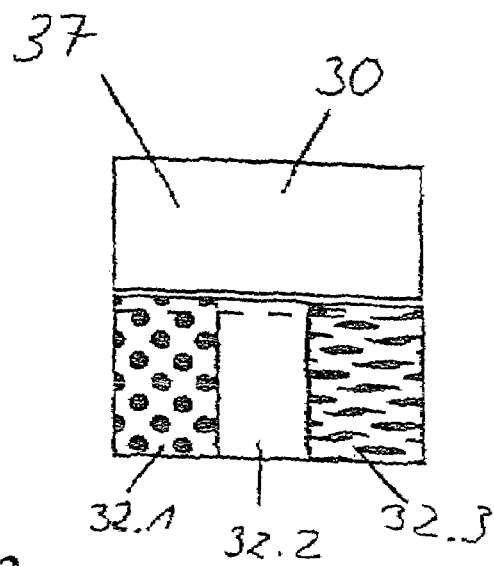
Figure 13:
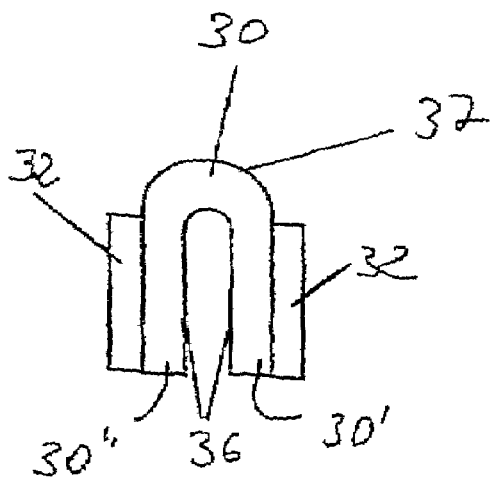
FIG. 13 shows a seventh example of a support which can be mounted on a measuring head, in two views.
Figure 13:
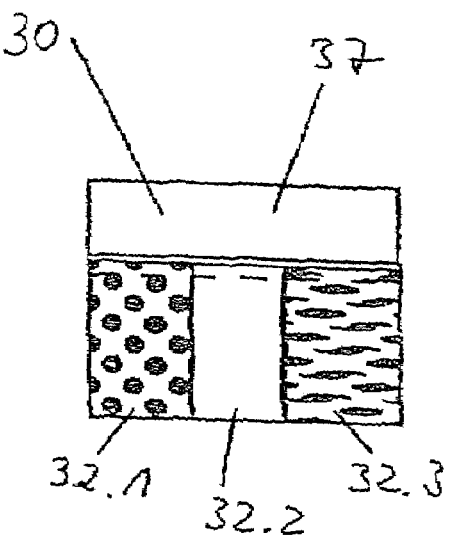

FIGS. 12 and 13 show further possibilities of how a support 30 can be constructed, only slightly modified U shapes having been represented here by way example.

Figure 14:
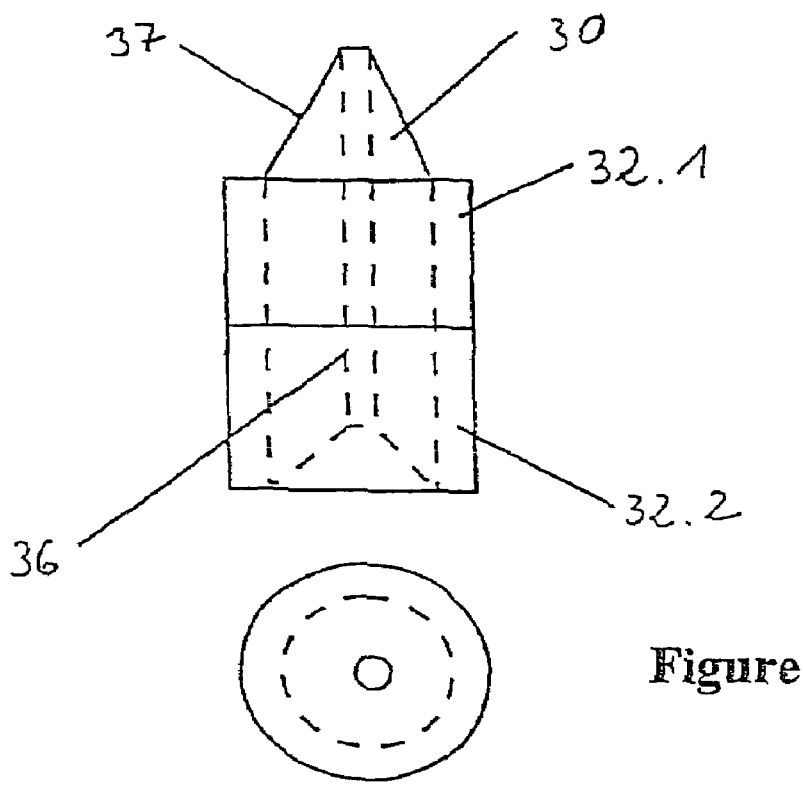
FIG. 14 shows an eighth example of a support which can be mounted on a measuring head, in two views.
Figure 15:
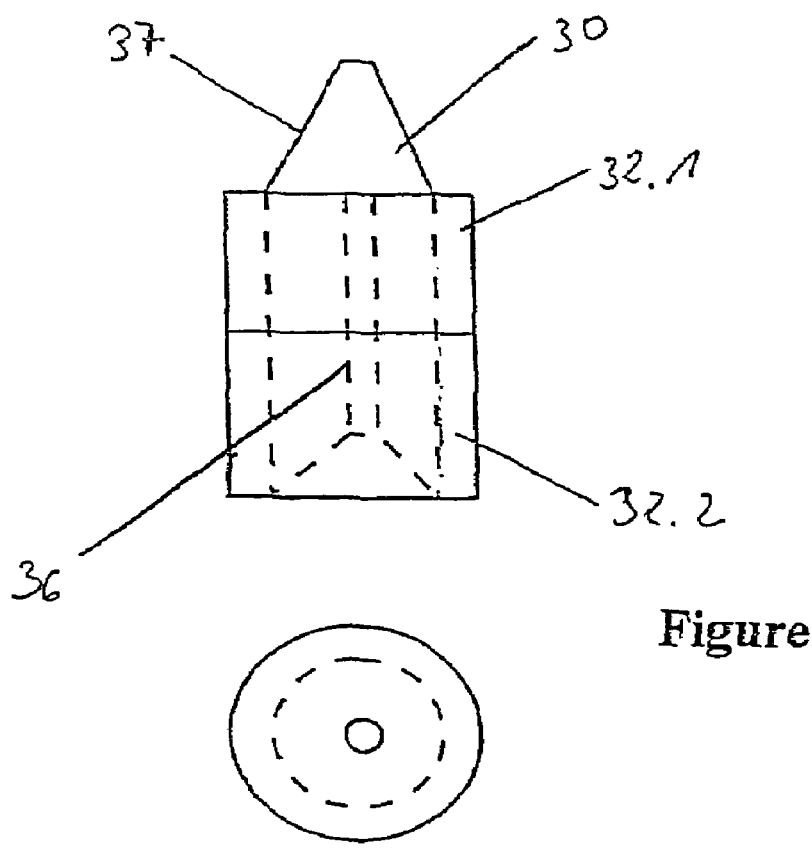
FIG. 15 shows a ninth example of a support which can be mounted on a measuring head, in two views.

FIGS. 14 and 15 show rotationally symmetrical supports 30 whose upper part is of conical construction, and in which the layers 32.1 and 32.2 containing fluorescing materials are arranged or constructed in the shape of a circular ring around the outer lateral surface of the support 30, if appropriate on an additional, appropriately constructed support, or directly on the surface.

The two examples of FIGS. 14 and 15 differ 10 only in the construction of the reflecting coating 36. In "both examples", the light is launched into and coupled out of the support 30 through conically recessed end faces.

Represented in FIG. 16 is a body 40 made from 15 an optically scattering material such as, for example, a polyester filled with titanium oxide, aluminum oxide or zirconium oxide, to which, in turn, layers 32.1 and 32.2 containing fluorescing materials are applied directly or on a flat substrate.

Such a body 40, which can also be designated as a diffuser plate, can have cutouts or cavities 42 which are dimensioned and arranged such that the body 40 can be mounted on a measuring head 1 as represented, for example, in FIG. 3. In this case, the exciting light is radiated into the body 40 by the optical fiber 3 and distributed there diffusely, as a result of which a uniform excitation of fluorescence is achieved in the layers 32 and at least a portion of the fluorescent light is redirected into the body 40, and directed from there into the optical fibers 16 and 15 onto the detectors 4 for the purpose of measuring the fluorescence intensity.

It is also possible that the fluorescent light can be launched into the optical fibers 15, 16 from an end face of the layer(s) 32, and can thereby be directed onto the detector(s) 4, 5.

Such a body 40 can, however, also consist of an optically transparent material which is provided on the exposed surfaces with a reflecting coating, and the surface of the body 40 is constructed in an optically scattering fashion in the region of the layers 32 containing fluorescing materials.

Figure 17:
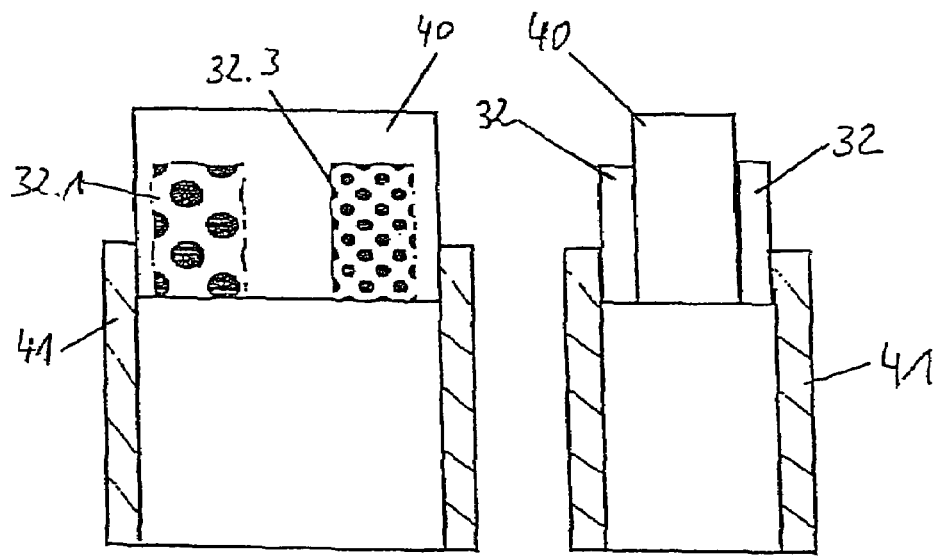
FIG. 17 shows a body which can be mounted on a measuring head.

A cap 41 with a body 40, which can be 5 constructed, in turn, as already set forth in the description of FIG. 16, is shown in FIG. 17, and on the body 40, in turn, at least one layer 32 containing a fluorescing material is arranged or constructed there. As was represented, for example, in FIG. 1, the cap 41 can then be mounted on a measuring head 1, and in this case the arrangement and alignment of the optical fibers 15 and 16 for the fluorescent light should be performed to correspond with those of the respective layers 32.1 or 32.3.

A further example of a body 40 which can already be constructed, as mentioned above, is represented in FIG. 18.

Such a body 40, can, in turn, easily be made available in a simple way as an exchangeable part, as is also the case for the cap 41 in accordance with FIG. 17 and the body 40 in accordance with FIG. 16.

Figure 18:
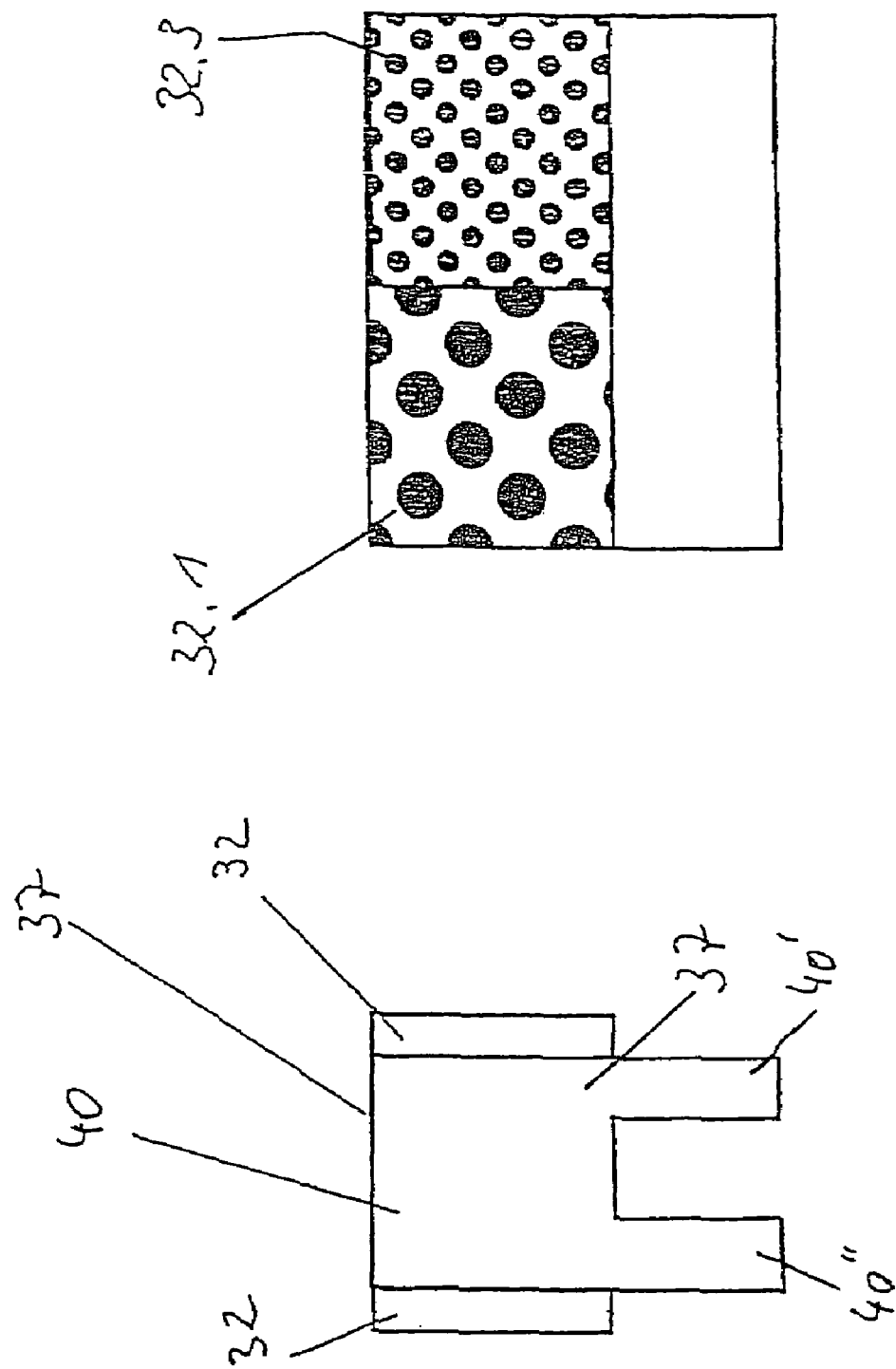
FIG. 18 shows a body which can be mounted on a measuring head.

If, as also represented in FIG. 3*a*, the body 40 according to FIG. 18 is mounted on a measuring head 1, the light of the light source 2 passes relatively accurately into the middle of the body 40 and is scattered there diffusely and fluorescence is excited in the layers 32.1 and 32.3 virtually simultaneously. The fluorescent light retro reflected into the body 40 passes via the limbs 40' and 40" of the body 40 and the optical fibers 15 via an optical system 25 onto a photo detector 4, it being possible for an optical filter 8 to be arranged upstream of the latter, and the evaluation of the measuring signals being carried out with the electronic system 9 integrated in the measuring head 1.

Figure 19:
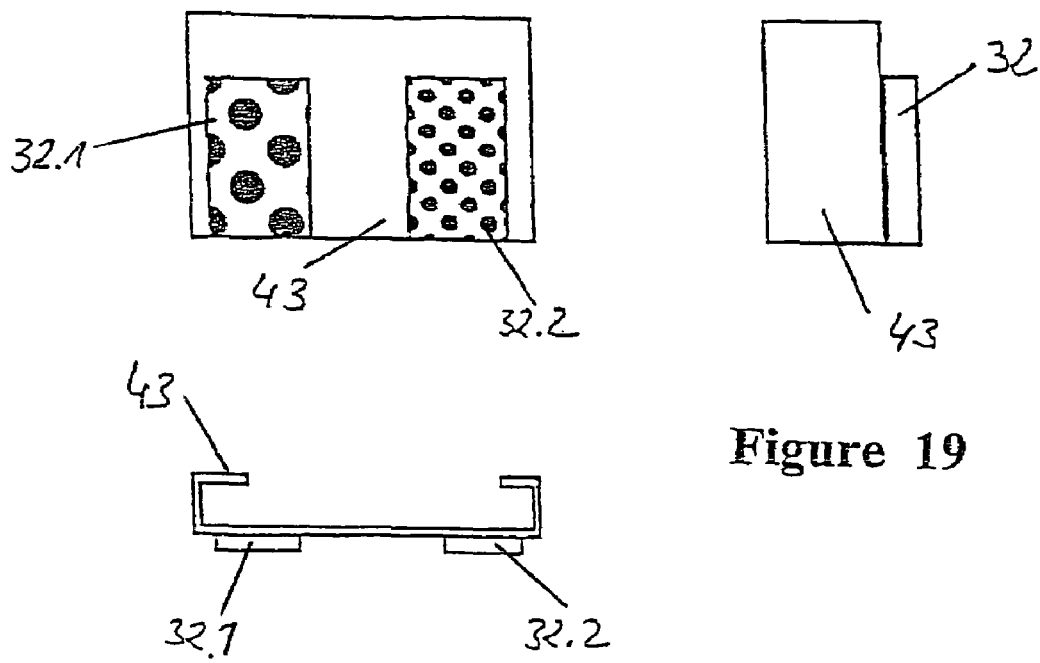
FIG. 19 shows a first holder for fluorescent layers, in three views.
Figure 20:
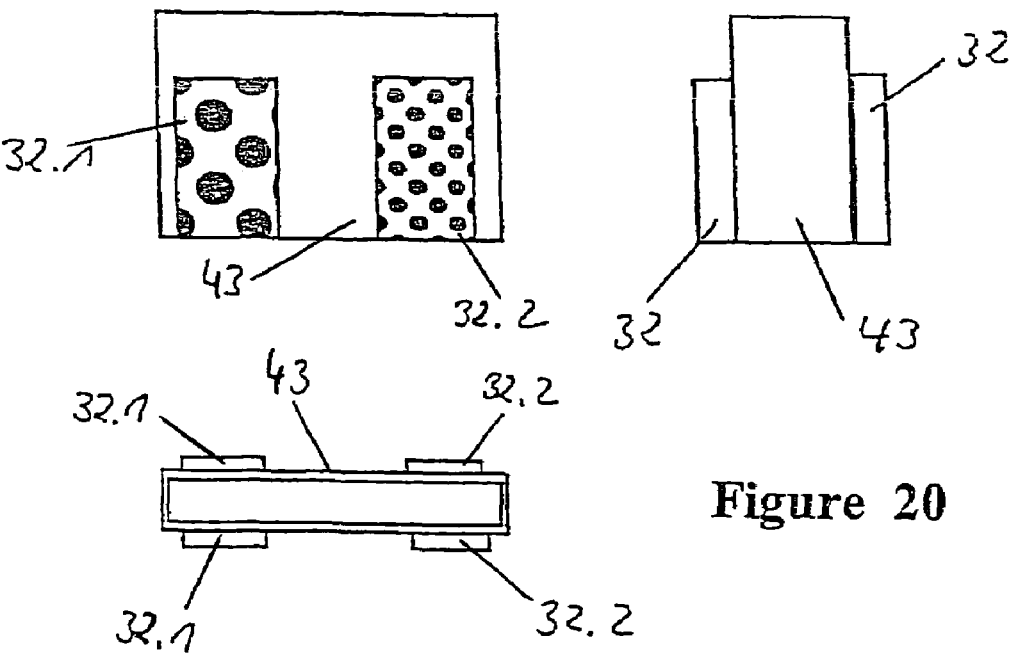
FIG. 20 shows a second holder for fluorescent layers in three views.

FIGS. 19 and 20 represent two examples of holders 43 on which it is possible to fasten layers 32.1 and 32.2 containing fluorescing materials. These layers 32.1 and 32.2 are preferably applied to a plane, flat, transparent substrate which can be fastened on the holder 43 in a self-closed fashion and/or with a binding agent.

A holder 43 thus prepared can then readily be 5 mounted and fastened on, for example, a body 40 which can, if appropriate, be a permanent component of a measuring head 1, as is represented in FIG. 3*a*.

Figure 21:
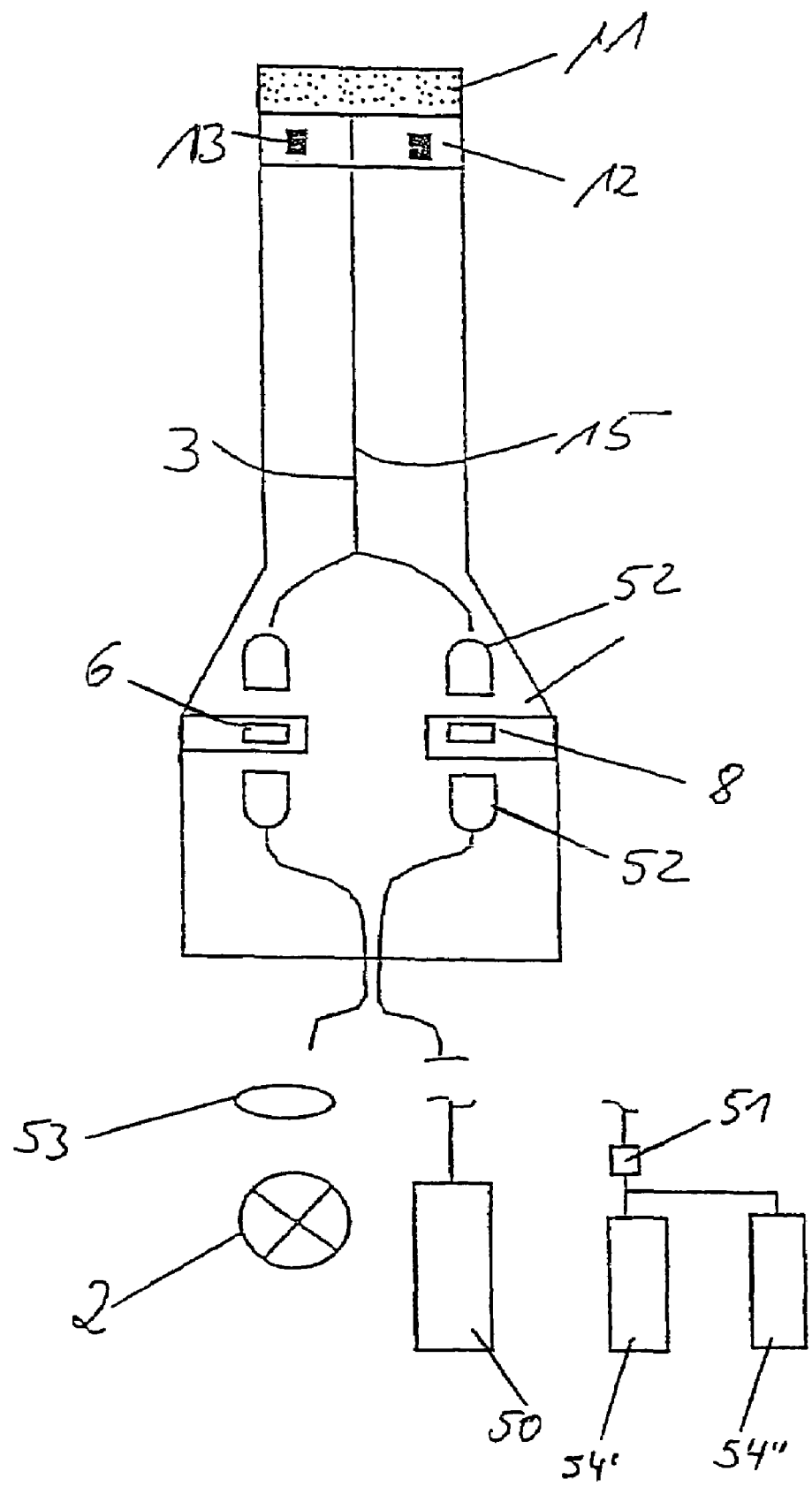
FIG. 21 shows a measuring head for measuring with wavelength resolution.

Represented in FIG. 21 is a further example of a measuring head 1 according to the invention, on whose upper tip there is arranged, in turn, a layer 11 in which at least one fluorescing material is contained. Arranged, in turn, below this layer 11 is a temperature sensor 13 and a heating element 12, the aim being, if required, to prevent the formation of condensate on the layer 11.

The exciting light is once again launched into an optical fiber 3 starting from the light source 2 via an optical system 53 and an exchangeable filter 6, and directed onto the layer 11. The excited fluorescent light passes via the optical fiber 15, the optical systems 52 and the exchangeable filter 8 into a spectrometer 50, for the purpose of wave length-resolved measurement, to different detectors 54' and 54" via an opt coupler 51.

Figure 22:
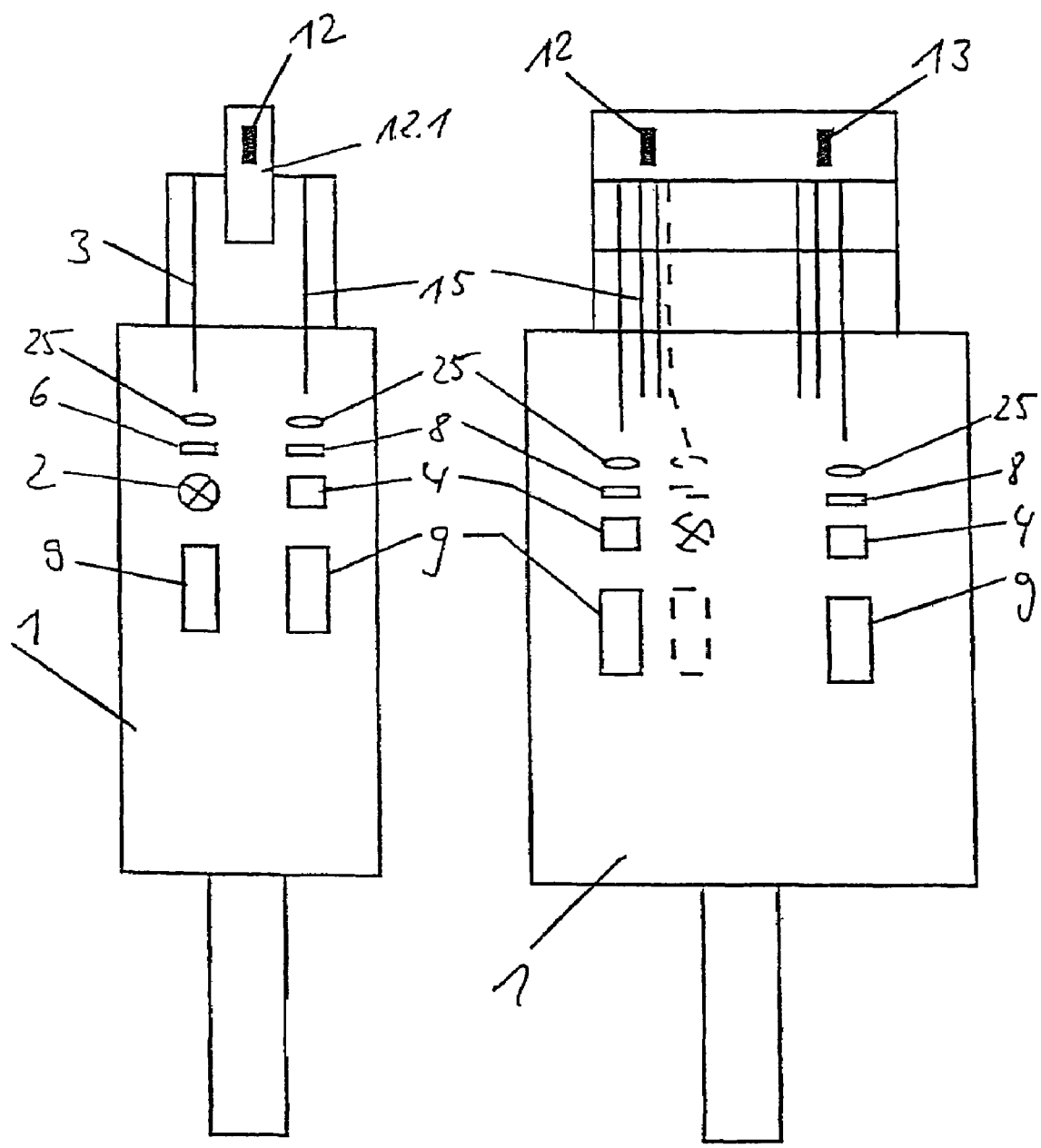
FIG. 22 shows a further measuring head in three views.

A further example of a measuring head 1 according to the invention is represented in FIG. 22, in two views. In this case, the exciting light of the light source 2 is launched only on one side into a limb 30' or 30" of a support 30 such as is represented in FIGS. 4 to 15, and coupled out again from the respective other limb 30' or 30" or both limbs 30' and 30", and directed onto detectors 4 in order to determine the fluorescence intensity.

What is claimed is:

1. A device for measuring fluorescence with at least two separate measurement channels excited by light comprising a single measuring head, the single measuring head comprising:

a) an upper measuring head region having a face designed to have at least one fluorescing material applied thereto, or be in contact with at least one fluorescing material, or with a support having at least one fluorescing material applied thereto;

b) at least one light source which emits light of at least one wavelength which excites at least one fluorescence, and thus, fluorescent light, in the at least one layer;

c) a plurality of optical conductors comprising:

at least one first and one second optical conductor directing the light from the at least one light source directly in to, or in the direction of, the fluorescing material;

the same optical conductors receiving the fluorescent light generated in the fluorescent layer onto the at least one detector; or i) at least one first optical conductor which directs the light from the at least one light source directly into or in the direction of the fluorescing material; and ii) at least one detector for measuring the intensity of the fluorescent light;

d) at least one second optical conductor receiving the fluorescent light generated in the fluorescing layer, the at least one second optical conductor directing the fluorescent light onto the at least one detector; and e) at least one detector for measuring the intensity of the fluorescent light generated in the fluorescing layer f) wherein the at least one first optical conductor is arranged to achieve measured values of the fluorescent light from the at least two channels in a single measurement head.

2. The device defined in claim 1, wherein the single measuring head contains at least two light sources and at least one detector, wherein the at least two light sources excite the fluorescence in different areas of the fluorescing material using the at least first and second optical conductor, and the single detector is able to receive reflected light from both areas using the same or two further optical conductors.

3. The device defined in claim 1, wherein the measuring head contains at least two light sources, at least one optical conductor, and at least one detector, whereupon the at least two light sources excite the fluorescence within a sensitive layer of the fluorescing material at different wavelengths using the at least optical conductor at the at least one detector is able to receive those two different wavelengths via the at least one optical conductor.

4. The device defined in claim 1, wherein the measuring head consists of one light source, two optical detectors, and a plurality of optical conductors, wherein the one light source excites the fluorescence within the sensitive layer or the fluorescing material using at least one of the plurality of optical conductors, and the two optical conductors receive reflected light from different areas of the sensitive layer using the same or at least two others of the plurality of optical conductors.

5. Device according to claim 1, wherein the measuring head consists of one light source, two optical detectors, and a plurality of optical conductors, wherein the one light source excites fluorescence within the sensitive layer of the fluorescing material using one of the plurality of optical conductors, and the two optical detectors are able to receive two different wavelengths of light through the same or two others of the plurality of optical conductors.

6. Device according to claim 1, wherein the measuring head has an upper region, which is at least partially bent.

7. Device according to claim 1, wherein at least one of a filter, a system of exchangeable filters, or a launching optical system is arranged between the light source and at least one first optical conductor.

8. Device according to claim 1, wherein at least one of the second optical conductors receiving the fluorescent light and the first optical conductors transmitting the exciting light from the light source are arranged in the shape of a ring, a circular arc or a star on an end of the measuring head, wherein at least some of the first optical conductors have an axis which is not parallel to the axis of at least some of the second optical conductors, with all of the first and the second optical conductors pointing towards the at least one layer containing fluorescing material.

9. Device according to claim 6, wherein at least one of the second optical conductors is arranged in an inner ring or first and second optical conductors are arranged in form of a ring with an alternating arrangement.

10. Device according to claim 1, wherein the at least one first and the at least one second optical conductors are inclined at different angles with their ends pointing towards the fluorescing layer.

11. Device according to claim 1, wherein there is arranged on an upper measuring head region a heater having a temperature sensor and a controller or regulator which is arranged in the measuring head and maintains a prescribable temperature at the fluorescing layer(s).

12. Device according to claim 1, wherein the support, which is transparent to exciting light and fluorescent light, has a surface which contains partially polished or reflecting surface regions or is surrounded by a medium of lower refractive index, and is mounted in an exchangeable fashion on the measuring head.

13. Device according claim 10, wherein exciting light is launched into the support with the aid of at least one optical conductor such that the exciting light is totally reflected at least in the region of the layer, and attenuated total reflection occurs.

14. Device according to claim 10, wherein the support is constructed in an elongated fashion in a plane.

15. Device according to claim 10, wherein the support is subdivided along its longitudinal axis into a plurality of regions.

16. Device according to claim 10, wherein, on an end face opposite and end face into which the exciting light can be launched, the support has an angular surface and a layer of the at least one layer which contains fluorescing material and at which the exciting and fluorescing light is reflected in the direction of a planar optical conductor constructed symmetrically relative to the support, and the light from the angular surface thereof is directed onto an end face arranged at the other end of an optical conductor, and from there at least fluorescent light is directed onto a detector via at least one of the optical conductors, the support and planar optical conductor being arranged at a spacing from one another or being optically separated into the region of the angular surface.

17. Device according to claim 10, wherein the support is of u-shaped construction comprising two limbs, the two limbs are optically separated from one another, and the exciting light can be launched into an end face of a limb via at least one additional optical conductor, and at least fluorescent light can be coupled out via the end face of the other limb into at least one further optical conductor, which at least one additional optical conductor and at least one further optical conductor are in addition to the at least one first and at least one second optical conductors.

18. Device according to claim 15, wherein the two limbs of the u-shaped support are connected in the shape of a bow, a wedge or a cone, or by means of an angular web.

19. Device according to claim 1, wherein at least one of the heating elements or temperature sensor elements are integrated into the support.

20. Device according to claim 1, wherein between one of the optical conductors and one of the at least one layers containing the fluorescing material, a transparent body made from optically scattering material is arranged or a body comprising a diffusely scattering surface is positioned facing the layer.

21. Device according to claim 18, wherein the body is formed from optically transparent material which contains light-scattering particles or a material in which a wavelength specific absorption occurs.

22. Device according to claim 1, wherein at least one further optical conductor directs reference light onto a further detector for detecting a reference signal.

23. Device according to claim 1, wherein an upper heated region is thermally insulated with respect to a lower region, in which lower region the light source(s) and the detector(s) are held.

24. Device according to claim 1, wherein said device is configured to detect fluorescence-quenching, fluid materials.

25. Device according to claim 1, wherein the support is configured to receive heating elements.

26. The device defined in claim 1, wherein the upper measuring head region having a face designed to have a fluorescing material applied thereto, or be in contact with a fluorescing material, or with a support having fluorescing material applied thereto, the fluorescing material comprising at least two different fluorescences;
  b) at least one light source which emits light of at least one wavelength which excites at least one of the two different fluorescences, and thus, fluorescent light, in each of the at one layer(s);
  c) at least one optical conductor which directs the light from the at least one light source directly into or in the direction of the two different fluoresences;
  d) at least one detector for measuring the intensity of the fluorescent light reflected from each of the two different fluorescences back through the at least one optical conductor.

27. A device for measuring fluorescence excited by light comprising:
  a) a support;
  b) at least one layer of a material applied to the support, the at least one layer of material having a planar fluorescing layer containing a fluorescing material;
  c) at least one light source which emits light of at least one wavelength which excites at least one fluorescence, and thus, fluorescent light, in the at least one layer;
  d) at least one first optical conductor which directs the light from the at least one light source directly into or in the direction of the at least one planar layer of material;
  e) at least one detector for measuring the intensity of the fluorescent light;
  f) at least one second optical conductor receiving the fluorescent light generated in the at least one layer, the at least one second optical conductor directing the fluorescent light onto the at least one detector; and
  g) a measuring head holding the at least one first optical conductor, the at least one second optical conductor, and the at least one light source;
  wherein the end faces of the at least one first optical conductor and the at least one second optical conductor are arranged relative to one another as a function of their numerical apertures and as a function of the at least one planar layer of material to achieve accurate local assignment of the measured values of the intensity of the fluorescent light, and wherein the at least one first optical conductor and the at least one second optical conductor are arranged as a bundle in the shape of a ring with the at least one first optical conductor arranged in the interior of the ring.

28. Device according to claim 27, wherein a part of the measuring head holds the outer ends of the optical conductors, and at least the part of the measuring head which holds the outer ends of the optical conductors is of flexible construction.

29. Device according to claim 27, wherein the measuring head has an upper region, which is at least partially bent.

30. Device according to claim 27, wherein at least one of a filter, a system of exchangeable filters or a launching optical system is arranged between the light source and at least one first optical conductor.

31. Device according to claim 27, wherein at least one of the optical conductors consist of conductors receiving the fluorescent light and optical conductors transmitting the exciting light from the light source are arranged in the shape of a ring, a circular arc or a star on an end of the measuring head pointing independent to each other towards the at least one layer containing fluorescing material.

32. Device according to claim 27, wherein at least one of the second optical conductors is arranged in an inner ring or first and second optical conductors are arranged in form of a ring with an alternating arrangement.

33. Device according to claim 27, wherein the at least one first and the at least one second optical conductors are inclined at different angles with their ends pointing towards the fluorescing layer.

34. Device according to claim 27, wherein there is arranged on an upper measuring head region a heater having a temperature sensor and a controller or regulator which is arranged in the measuring head and maintains a prescribable temperature at the fluorescing layer(s).

35. Device according to claim 27, wherein the support, which is transparent to exciting light and fluorescent light, has a surface which contains partially polished or reflecting surface regions or is surrounded by a medium of lower refractive index, and is mounted in an exchangeable fashion on the measuring head.

36. Device according claim 33, wherein exciting light is launched into the support with the aid of at least one optical conductor such that the exciting light is totally reflected at least in the region of the layer, and attenuated total reflection occurs.

37. Device according to claim 33, wherein the support is constructed in an elongated fashion in a plane.

38. Device according to claim 33, wherein the support is subdivided along its longitudinal axis into a plurality of regions.

39. Device according to claim 33, wherein, on an end face opposite an end face into which the exciting light can be launched, the support has an angular surface and a layer of the at least one layer which contains fluorescing material and at which the exciting and fluorescing light is reflected in the direction of a planar optical conductor constructed symmetrically relative to the support, and the light from the angular surface thereof is directed onto an end face arranged at the other end of an optical conductor, and from there at least fluorescent light is directed onto a detector via at least one of the optical conductors, the support and planar optical conductor being arranged at a spacing from one another or being optically separated into the region of the angular surface.

40. Device according to claim 33, wherein the support is of u-shaped construction comprising two limbs, the two limbs are optically separated from one another, and the exciting light can be launched into an end face of a limb via at least one additional optical conductor, and at least fluorescent light can be coupled out via the end face of the other limb into at least one further optical conductor, which at least one additional optical conductor and at least one further optical conductor are in addition to the at least one first and at least one second optical conductors.

41. Device according to claim 38, wherein the two limbs of the u-shaped support are connected in the shape of a bow, a wedge or a cone, or by means of an angular web.

42. Device according to claim 33, wherein at least one of heating elements or temperature sensor elements are integrated into the support.

43. Device according to claim 33, wherein between one of the optical conductors and one of the at least one layers containing the fluorescing material, a transparent body made from optically scattering material is arranged or a body comprising a diffusely scattering surface is positioned facing the layer.

44. Device according to claim 41, wherein the body is formed from optically transparent material, which contains light-scattering particles, or a material in which a wavelength specific absorption occurs.

45. Device according to claim 33, wherein at least one further optical conductor directs reference light onto a further detector for detecting a reference signal.

46. Device according to claim 33, wherein an upper heated region is thermally insulated with respect to a lower region, in which lower region the light source(s) and the detector(s) are held.

47. Device according to claim 33, wherein said device is configured to detect fluorescence-quenching, fluid materials.

48. Device according to claim 33, wherein the support is configured to receive heating elements.

* * * * *